United States Patent
Losey et al.

(10) Patent No.: US 11,945,870 B2
(45) Date of Patent: *Apr. 2, 2024

(54) IMMUNOMODULATORY IL-2 AGENTS IN COMBINATION WITH IMMUNE CHECKPOINT INHIBITORS

(71) Applicant: Mural Oncology, Inc., Waltham, MA (US)

(72) Inventors: Heather C. Losey, Waltham, MA (US); Jared Lopes, Waltham, MA (US); Raymond J. Winquist, Waltham, MA (US)

(73) Assignee: Mural Oncology, Inc., Waltham, MA (US)

( * ) Notice: Subject to any disclaimer, the term of this patent is extended or adjusted under 35 U.S.C. 154(b) by 62 days.

This patent is subject to a terminal disclaimer.

(21) Appl. No.: 17/568,281

(22) Filed: Jan. 4, 2022

(65) Prior Publication Data

US 2022/0227868 A1    Jul. 21, 2022

Related U.S. Application Data

(63) Continuation of application No. 17/072,725, filed on Oct. 16, 2020, now Pat. No. 11,248,050.

(60) Provisional application No. 62/916,936, filed on Oct. 18, 2019.

(51) Int. Cl.
   *C07K 16/00*  (2006.01)
   *A61P 35/00*  (2006.01)
   *C07K 16/28*  (2006.01)
   *A61K 39/00*  (2006.01)

(52) U.S. Cl.
   CPC .......... *C07K 16/2818* (2013.01); *A61P 35/00* (2018.01); *C07K 16/2827* (2013.01); *A61K 2039/545* (2013.01)

(58) Field of Classification Search
   CPC .............. A61K 38/16; A61K 2039/545; C07K 16/2818; A61P 35/00
   See application file for complete search history.

(56) References Cited

U.S. PATENT DOCUMENTS

| | | | |
|---|---|---|---|
| 9,844,582 B2 | 12/2017 | Wittrup et al. | |
| 2014/0234962 A1 | 8/2014 | Alvarez | |
| 2016/0175458 A1 | 6/2016 | Alvarez et al. | |
| 2017/0233448 A1* | 8/2017 | Malek | C07K 14/55 424/85.2 |

FOREIGN PATENT DOCUMENTS

| | | |
|---|---|---|
| WO | WO 2013184942 A1 | 12/2013 |
| WO | WO 2014170032 A1 | 10/2014 |
| WO | WO 2016100788 A1 | 6/2016 |
| WO | WO 2019094916 A1 | 5/2019 |
| WO | WO 2020249687 A1 | 12/2020 |
| WO | WO 2020249693 A1 | 12/2020 |

OTHER PUBLICATIONS

Alkermes PLC Securities and Exchange Commission Form 8-K Current report filing, Internet Citation, Jan. 7, 2019. http://pdf.secdatabase.com/1739/0001564590-19-000274.pdf.

Anonymous: "Alkermes Initiates Clinical Study of ALKS 4230 Administered Subcutaneously in Patients With Advanced Solid Tumors", News from Alkermes, May 19, 2019, XP002800274, https://www.prnewswire.com/news- releases/alkermes-initiates-clinical-study-of-alks-4230-administered-subcutaneously-in-advanced-solid-tumors-300801629.html.

Anonymous: "A Dose Escalation and Cohort Expansion Study of Subcutaneously-Administered Cytokine ALKS 4230) (Nemvaleukin Alfa) as a Single Agent and in Combination With Anti-PD-1-Antibody (Pembrolizumab) in Subjects With Select Advanced or Metastatic Solid Tumors (ARTISTRY-2)", ClinicalTrials.gov, Dec. 2019. https://clinicaltrials.gov/ct/2/show/NCT03861793.

Charych et al., "NKTR-214, an Engineered Cytokine with Biased IL2 Receptor Binding, Increased Tumor Exposure, and Marked Efficacy in Mouse Tumor Models", *Clinical Cancer Search*, 22(3):680-690, 2016.

International Preliminary Report on Patentability for International Application No. PCT/EP2020/66234, dated Dec. 23, 2021, 14 pages.

International Preliminary Report on Patentability for International Application No. PCT/IB2020/000860, dated Apr. 28, 2022, 9 pages.

International Search Report and Written Opinion for International Application No. PCT/EP2020/066234, dated Sep. 24, 2020, 20 pages.

International Search Report and Written Opinion for International Application No. PCT/EP2020/066266, dated Sep. 30, 2020, 12 pages.

International Search Report and Written Opinion for International Application No. PCT/IB2020/000860, dated Feb. 25, 2021, 13 pages.

Lopes et al., "Ex vivo expansion and activation of human lymphocytes with a selective activator of effector cells", *Cancer Research*, vol. 75, Supplement 15, 2015. Abstract 3158. https://doi.org/10.1158/1538-7445.AM2015-3158.

Lopes et al., "Characterization of the pharmacodynamic immune response to a novel immunotherapeutic agent, ALKS 4230, in mice and non-human primates", *Cancer Research*, vol. 77, Supplement 13, Jul. 2017. Abstract 2663, https://doi.org/10.1158/1538-7445.AM2017-2663.

(Continued)

*Primary Examiner* — Jeanette M Lieb
(74) *Attorney, Agent, or Firm* — Fish & Richardson P.C.

(57) ABSTRACT

The invention provides compositions and methods of treating cancer in a patient with a combination therapy comprising a fusion protein of SEQ ID NO: 1 in combination with an immune checkpoint inhibitor. Preferably the patient has failed to achieve complete or partial response with prior or ongoing treatment with an immune checkpoint inhibitor.

19 Claims, 14 Drawing Sheets

Specification includes a Sequence Listing.

(56) References Cited

OTHER PUBLICATIONS

Lopes et al., "ALKS-4230: a novel engineered IL-2 fusion protein with an improved cellular selectivity profile for cancer immunotherapy", *Journal for Immunotherapy of Cancer*, vol. 8, No. 1, Apr. 2020.

Losey, et al. "Efficacy of ALKS 4230, a novel immunotherapeutic agent, in murine syngeneic tumor models alone and in combination with immune checkpoint inhibitors", *Cancer Research*, vol. 77, Supplement 13, 2017. Abstract 591. https://doi.org/10.1158/1538-7445.AM2017-591.

Pfannenstiel et al., "A novel, individualized xenograft model of cancer immunotherapy and tumor growth inhibition by ALKS 4230", *Journal for Immunotherapy of Cancer*, vol. 5, Supplement 2, Nov. 2017. Abstract P351.

Powderly, J., "Phase 1/2 study of subcutaneously administered ALKS 4230 as monotherapy and in combination with pembrolizumab in patients with advanced solid tumors: ARTISTRY-2", *Journal for Immunotherapy of Cancer*, 2020, Abstract 373, 8(Suppl. 3): A1-A559 (A227).

Sun et al., "First-in-human dose selection for ALKS 4230, an investigational immunotherapeutic agent", *Experimental and Molecular Therapeutics*, vol. 77, Supplement 13, Jul. 2017. Abstract 4088. https://doi.org/10.1158/1538-7445.AM2017-4088.

Sun et al., "P425 Pharmacokinetics and pharmacodynamic effects of ALKS 4230, an investigational immunotherapeutic agent, in cynomolgus monkeys after intravenous and subcutaneous administration", *Journal for Immunotherapy of Cancer*, vol. 6, Supplement 1, Nov. 2018.

Vaishampayan et al. "Intravenous administration of ALKS 4230 as monotherapy and in combination with pembrolizumab in a phase I study of patients with advanced solid tumors", *Journal of Clinical Oncology*, vol. 37, Supplement 15, Abstract, May 2019.

Vaishampayan et al., "ALKS 4230, an engineered IL-2 fusion protein, in monotherapy dose-escalation and combination therapy with pembrolizumab in patients with solid tumors: ARTISTRY-1 trial", *Journal of Immunotherapy of Cancer*, vol. 7, Supplement 1, pp. 243-244, Nov. 2019. Abstract P447. https://doi.org/10.1186/S40425-019-0763-1.

Wang et al., "Structure of the Quaternary Complex of Interleukin-2 with Its, and $\alpha$, $\beta$ and $\gamma_c$ Receptors", *Science*, 310:1159-1163, 2005.

\* cited by examiner

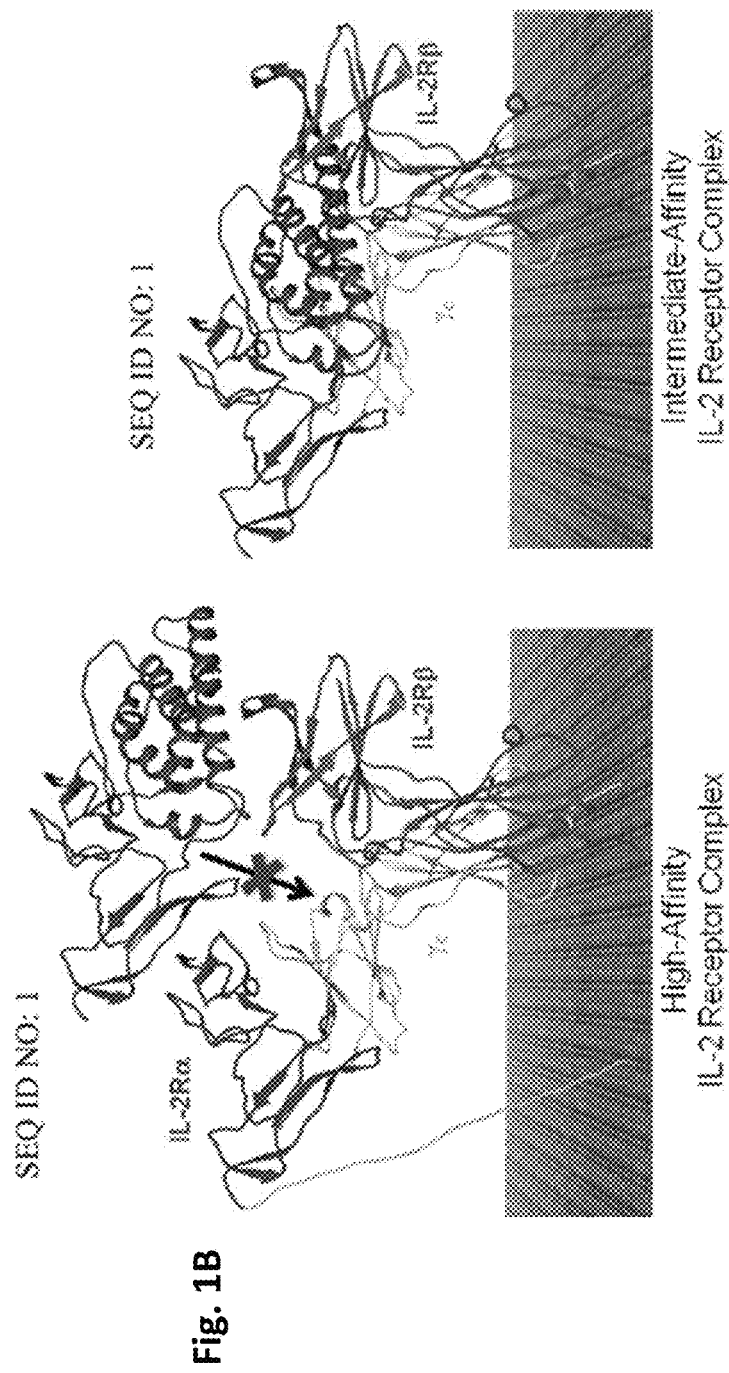
Fig. 1A
Fig. 1B

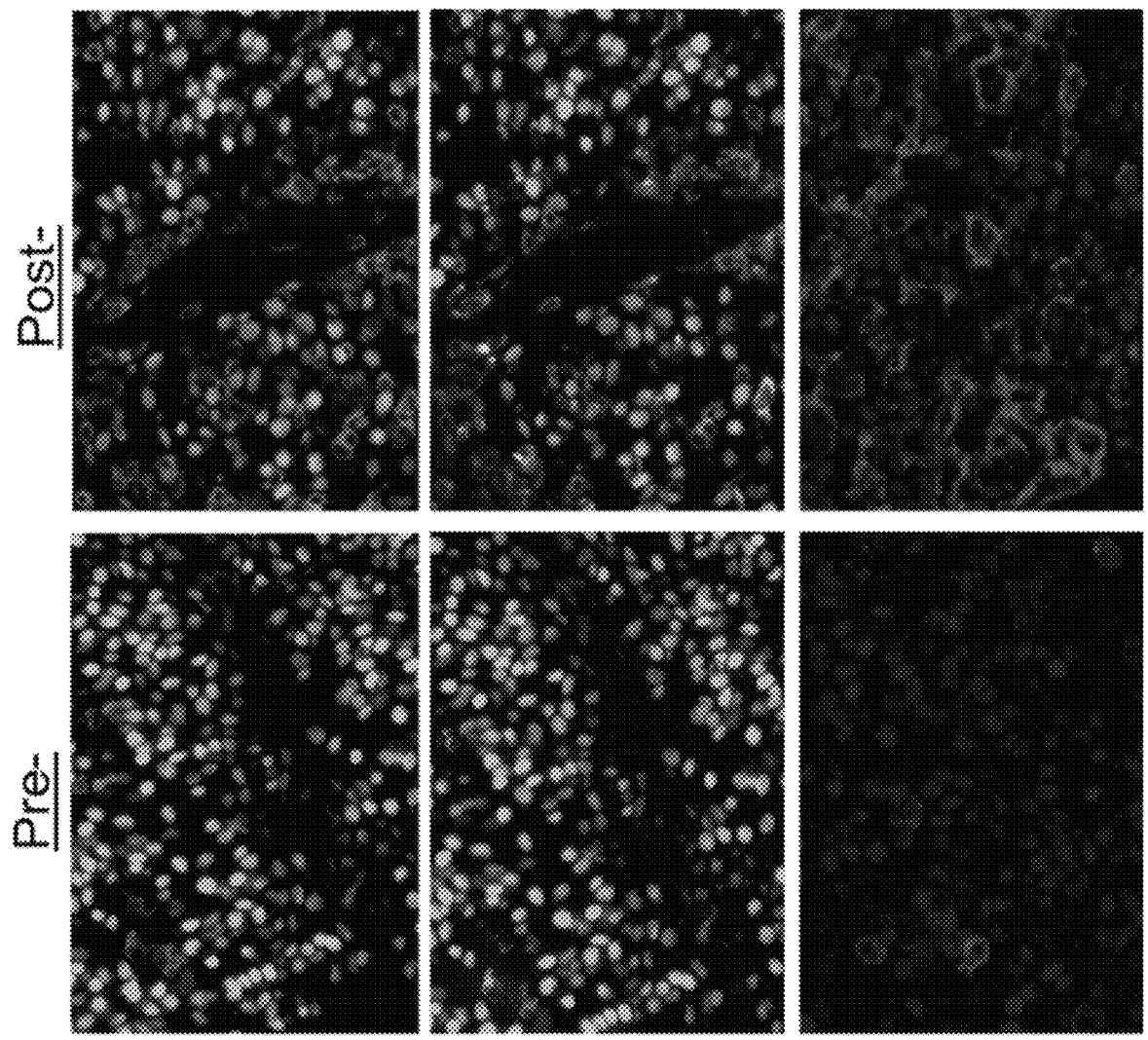

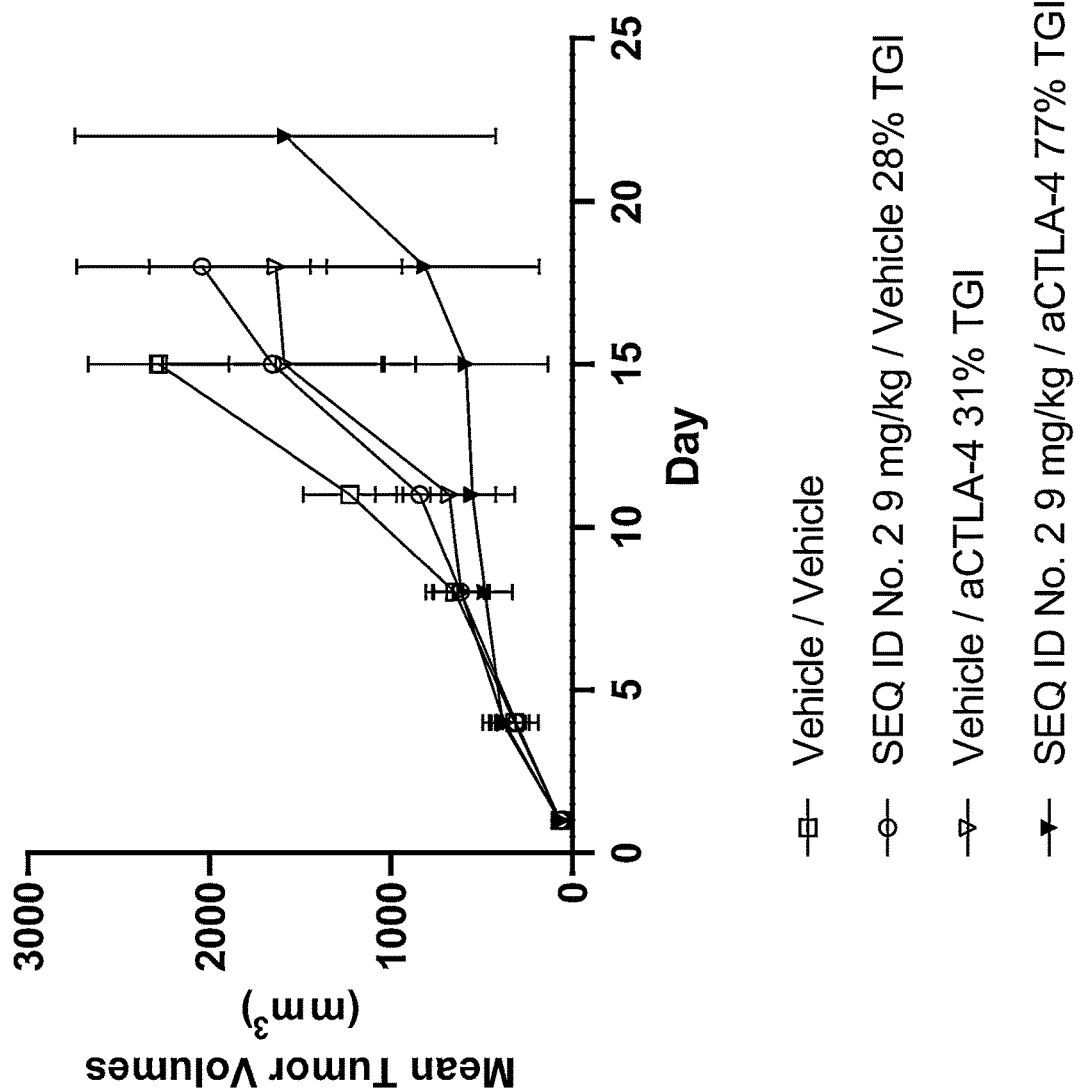

SEQUENCE LISTING

```
<160> NUMBER OF SEQ ID NOS: 2

<210> SEQ ID NO 1
<211> LENGTH: 303
<212> TYPE: PRT
<213> ORGANISM: Artificial Sequence
<220> FEATURE:
<223> OTHER INFORMATION: cpIL-2:IL-2Ralpha

<400> SEQUENCE: 1

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
    50                  55                  60

Thr Lys Lys Thr Gln Leu Gln Leu Glu His Leu Leu Leu Asp Leu Gln
65                  70                  75                  80
```

Met Ile Leu Asn Gly Ile Asn Asn Tyr Lys Asn Pro Lys Leu Thr Arg
            85                  90                  95

Met Leu Thr Phe Lys Phe Tyr Met Pro Lys Lys Ala Thr Glu Leu Lys
                100                 105                 110

His Leu Gln Cys Leu Glu Glu Glu Leu Lys Pro Leu Glu Glu Val Leu
            115                 120                 125

Asn Leu Ala Gln Gly Ser Gly Gly Gly Ser Glu Leu Cys Asp Asp Asp
        130                 135                 140

Pro Pro Glu Ile Pro His Ala Thr Phe Lys Ala Met Ala Tyr Lys Glu
145                 150                 155                 160

Gly Thr Met Leu Asn Cys Glu Cys Lys Arg Gly Phe Arg Arg Ile Lys
                165                 170                 175

Ser Gly Ser Leu Tyr Met Leu Cys Thr Gly Asn Ser Ser His Ser Ser
                180                 185                 190

Trp Asp Asn Gln Cys Gln Cys Thr Ser Ser Ala Thr Arg Asn Thr Thr
            195                 200                 205

Lys Gln Val Thr Pro Gln Pro Glu Glu Gln Lys Glu Arg Lys Thr Thr
        210                 215                 220

Glu Met Gln Ser Pro Met Gln Pro Val Asp Gln Ala Ser Leu Pro Gly
225                 230                 235                 240

His Cys Arg Glu Pro Pro Trp Glu Asn Glu Ala Thr Glu Arg Ile
                245                 250                 255

Tyr His Phe Val Val Gly Gln Met Val Tyr Tyr Gln Cys Val Gln Gly
                260                 265                 270

Tyr Arg Ala Leu His Arg Gly Pro Ala Glu Ser Val Cys Lys Met Thr
        275                 280                 285

His Gly Lys Thr Arg Trp Thr Gln Pro Gln Leu Ile Cys Thr Gly
    290                 295                 300

<210> SEQ ID NO 2
<211> LENGTH: 309
<212> TYPE: PRT
<213> ORGANISM: Artificial Sequence
<220> FEATURE:
<223> OTHER INFORMATION: murine cpIL-2:IL-2Ralpha

<400> SEQUENCE: 2

Ser Lys Ser Phe Gln Leu Glu Asp Ala Glu Asn Phe Ile Ser Asn Ile
1               5                   10                  15

Arg Val Thr Val Val Lys Leu Lys Gly Ser Asp Asn Thr Phe Glu Cys
            20                  25                  30

Gln Phe Asp Asp Glu Ser Ala Thr Val Val Asp Phe Leu Arg Arg Trp
        35                  40                  45

Ile Ala Phe Cys Gln Ser Ile Ile Ser Thr Ser Pro Gln Gly Gly Ser
    50                  55                  60

Ser Ser Thr Gln Gln Gln Gln His Leu Glu Gln Leu Leu Met Asp
65                  70                  75                  80

Leu Gln Glu Leu Leu Ser Arg Met Glu Asn Tyr Arg Asn Leu Lys Leu
                85                  90                  95

Pro Arg Met Leu Thr Phe Lys Phe Tyr Leu Pro Lys Gln Ala Thr Glu
                100                 105                 110

Leu Lys Asp Leu Gln Cys Leu Glu Asp Glu Leu Gly Pro Leu Arg His
            115                 120                 125

Val Leu Asp Leu Thr Gln Gly Ser Gly Gly Gly Ser Glu Leu Cys Leu
        130                 135                 140

```
Tyr Asp Pro Pro Glu Val Pro Asn Ala Thr Phe Lys Ala Leu Ser Tyr
145                 150                 155                 160

Lys Asn Gly Thr Ile Leu Asn Cys Glu Cys Lys Arg Gly Phe Arg Arg
                165                 170                 175

Leu Lys Glu Leu Val Tyr Met Arg Cys Leu Gly Asn Ser Trp Ser Ser
            180                 185                 190

Asn Cys Gln Cys Thr Ser Asn Ser His Asp Lys Ser Arg Lys Gln Val
        195                 200                 205

Thr Ala Gln Leu Glu His Gln Lys Glu Gln Gln Thr Thr Thr Asp Met
    210                 215                 220

Gln Lys Pro Thr Gln Ser Met His Gln Glu Asn Leu Thr Gly His Cys
225             230                 235                 240

Arg Glu Pro Pro Pro Trp Lys His Glu Asp Ser Lys Arg Ile Tyr His
            245                 250                 255

Phe Val Glu Gly Gln Ser Val His Tyr Glu Cys Ile Pro Gly Tyr Lys
            260                 265                 270

Ala Leu Gln Arg Gly Pro Ala Ile Ser Ile Cys Lys Met Lys Cys Gly
        275                 280                 285

Lys Thr Gly Trp Thr Gln Pro Gln Leu Thr Cys Val Asp Gly Ser His
    290                 295                 300

His His His His His
305
```

IMMUNOMODULATORY IL-2 AGENTS IN COMBINATION WITH IMMUNE CHECKPOINT INHIBITORS

RELATED APPLICATIONS

This application is a continuation of U.S. patent application Ser. No. 17/072,725, filed Oct. 16, 2020, which claims the benefit of U.S. Provisional Application No. 62/916,936, filed Oct. 18, 2019, the entire disclosures of which are hereby incorporated by reference.

BACKGROUND OF THE INVENTION

The fusion protein of SEQ ID NO: 1 is a human interleukin-2 (IL-2) variant fusion protein designed for selective binding of the intermediate-affinity interleukin-2 (IL-2) receptor, IL-2Rβγ. The selectivity of the fusion protein of SEQ ID NO: 1 is achieved through the stable fusion of circularly permuted (cp) IL-2 fused to the IL-2Rα chain (CD25) of the IL-2 receptor.

The fusion protein of SEQ ID NO: 1 has advantages over native IL-2 as a therapeutic in that its selective targeting and activation of IL-2Rβγ results in the selective activation of subsets of CD8+ cells and NK cells, which can drive anti-tumor immune responses. The administration of the fusion protein of SEQ ID NO:1 is beneficial to cancer patients as it reduces the immune suppressing effects of regulatory T-cells such as CD4+ T cells, while increasing CD8+ memory T-cells, thereby recruiting the patient's own immune system to eliminate cancer cells. The fusion protein of SEQ ID NO: 1 also exhibits lasting effects following administration, thereby further improving the patient's response to the treatment.

Immune checkpoint proteins regulate T cell function in the immune system. T cells play a central role in cell-mediated immunity. Checkpoint proteins interact with specific ligands that send a signal into the T cell and essentially switch off or inhibit T cell function. Cancer cells take advantage of this system by driving high levels of expression of checkpoint proteins on their surface that results in control of the T cells expressing checkpoint proteins on the surface of regulatory T cells that enter the tumor microenvironment, thus suppressing the anticancer immune response. As such, inhibition of checkpoint proteins would result in restoration of T cell function and an immune response to the cancer cells.

Examples of immune checkpoint proteins include, but are not limited to CTLA-4, PDL1 (B7-H1, CD274), PDL2 (B7-DC, CD273), PD1, B7-H3 (CD276), B7-H4 (B7-S1, B7x, VCTN1), BTLA (CD272), HVEM, TIM3 (HAVcr2), GAL9, LAG3 (CD223), VISTA, KIR, 2B4 (CD244; belongs to the CD2 family of molecules and is expressed on all NK, γδ, and memory CD8+ (αβ) T cells), CD160 (also referred to as BY55), CGEN-15049, CHK 1 and CHK2 kinases, OX40, A2aR and various B-7 family ligands. Immune checkpoint inhibitors that have received accelerated approval from the U.S. Food and Drug Administration for cancer include ipilimumab (YERVOY®), pembrolizumab (KEYTRUDA®), atezolizumab (TECENTRIQ®), durvalumab (IMFINZ®), avelumab (BAVENCIO®), and nivolumab (OPDIVO®). YERVOY® is a monoclonal antibody that targets CTLA-4 on the surface of T cells and is approved for the treatment of melanoma. KEYTRUDA® targets PD-L1 and is used to treat melanoma and non-small cell lung cancer. OPDIVO® also targets PD-1 and is approved for treatment of melanoma, renal cell carcinoma, and non-small cell lung cancer.

Although the clinical studies with, for example, nivolumab and pembrolizumab have demonstrated antitumor activity and established the efficacy, activity, and benefits with anti-PD-1 therapy in the recurrent metastatic platinum-experienced HNSCC population, for example, the response rates remain low, and the numbers of patients who relapse or fail to achieve complete responses remain in the high majority of 85% or more. As patients with HNSCC suffer tremendous morbidity and mortality with this disease, and the efficacy of any single-agent chemotherapy remains low with no proven salvage options in this population that fails anti PD-1 therapy, there is an exceptionally high unmet need to discover new therapies or effective combination immunotherapy to enhance, improve, or restore the responses to anti-PD-1 therapy.

SUMMARY OF THE INVENTION

The invention provides, compositions, methods and combination treatment regimens for treating cancer in a patient by administering to the patient a combination of a fusion protein of SEQ ID NO: 1, and an immune checkpoint inhibitor such as an inhibitor that blocks receptor/ligand pairs such as CTLA-4 or PD-1.

Preferably, the methods of the invention comprise: i) administering to the patient a therapeutically effective amount of the fusion protein of SEQ ID NO: 1; and ii) administering to the patient a therapeutically effective amount of an immune checkpoint inhibitor; wherein step (i) may be carried out before, after or simultaneously with step (ii) wherein the combination treatment regimen treats cancer in the patient. Preferably, the patient has previously failed to achieve complete or partial response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria; preferably. Preferably wherein the patient has previously failed to achieve complete response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria. Preferably wherein the immune checkpoint inhibitor is an anti-PD-1 antibody or an anti PD-L1 antibody. Preferably wherein the immune checkpoint inhibitor is pembrolizumab. Preferably wherein the immune checkpoint inhibitor is an anti-CTLA4 antibody. Preferably wherein the immune checkpoint inhibitor is ipilimumab. Preferably wherein the fusion protein of SEQ ID NO: 1 is administered parenterally to the patient. Preferably wherein a therapeutically effective amount of SEQ ID NO: 1 is a dose of SEQ ID NO: 1 of about 0.1 µg/kg, 0.3 µg/kg, 1 µg/kg, 3 µg/kg, 3.5 µg/kg, 4 µg/kg, 4.5 µg/kg, 5 µg/kg, 5.5 µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg, or 14.5 µg/kg.

Preferably the methods of the invention also provides combination treatment regimens for treating cancer in a patient comprising: i) administering to the patient a therapeutically effective amount of variant of the fusion protein of SEQ ID NO: 1 wherein the variant has an amino acid sequence that is about 80%, 85%, 90%, 91%, 92%, 93%, 94%, 95%, 96%, 97%, 98%, or 99% identical to SEQ ID NO: 1 over a contiguous stretch of from about 20% to 100% of the full length SEQ ID NO: 1; and ii) administering to the patient a therapeutically effective amount of an immune checkpoint inhibitor; wherein step (i) carried out before, after or simultaneously with step (ii). Preferably, the patient has previously failed to achieve complete or partial response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria. Preferably wherein the patient has previously failed to achieve complete response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria. Preferably wherein the immune checkpoint inhibitor is an anti-PD-1 antibody or an anti PD-L1 antibody. Preferably wherein the immune checkpoint inhibitor is pembrolizumab. Preferably wherein the immune checkpoint inhibitor is an anti-CTLA4 antibody. Preferably wherein the immune checkpoint inhibitor is ipilimumab. Preferably wherein the fusion protein of SEQ ID NO: 1 is administered parenterally to the patient. Preferably wherein a therapeutically effective amount of SEQ ID NO: 1 is a dose of SEQ ID NO: 1 of about 0.1 µg/kg, 0.3 µg/kg, 1 µg/kg, 3 µg/kg, 3.5 µg/kg, 4 µg/kg, 4.5 µg/kg, 5 µg/kg, 5.5 µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg, or 14.5 µg/kg.

In another aspect, the disclosure provides a method of treating cancer in a patient in need thereof, the method comprising:
i) administering to the patient a therapeutically effective amount of the fusion protein of SEQ ID NO: 1, or a variant thereof; and
ii) administering to the patient a therapeutically effective amount of an immune checkpoint inhibitor;
wherein step (i) is carried out before, after or simultaneously with step (ii),
wherein the patient has previously failed to achieve complete or partial response to prior treatment or to ongoing treatment with an immune checkpoint inhibitor, and
wherein the variant fusion protein is at least 80% identical to full length SEQ ID NO: 1.

In an embodiment, the patient has previously failed to achieve complete or partial response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria.

In an embodiment, the patient has previously failed to achieve complete response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria.

In an embodiment, the immune checkpoint inhibitor is an anti-PD-1 antibody or an anti PD-L1 antibody. In an embodiment, the immune checkpoint inhibitor is pembrolizumab.

In an embodiment, the immune checkpoint inhibitor is an anti-CTLA4 antibody. In an embodiment, the immune checkpoint inhibitor is ipilimumab.

In an embodiment, the fusion protein of SEQ ID NO: 1 or variant thereof is administered parenterally to the patient. In an embodiment, the fusion protein of SEQ ID NO: 1 or variant thereof is administered intravenously to the patient. In an embodiment, the fusion protein of SEQ ID NO: 1 or variant thereof is administered subcutaneously to the patient.

In an embodiment, a therapeutically effective amount of the fusion protein of SEQ ID NO: 1 or variant thereof is a dose of the fusion protein of SEQ ID NO: 1 or variant thereof of about 0.1 µg/kg, 0.3 µg/kg, 1 µg/kg, 3 µg/kg, 3.5 µg/kg, 4 µg/kg, 4.5 µg/kg, 5 µg/kg, 5.5 µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg, or 14.5 µg/kg.

In an embodiment, the fusion protein of SEQ ID NO: 1 or variant thereof is administered to the patient at a dose of about 3 µg/kg. In an embodiment, the fusion protein of SEQ ID NO: 1 or variant thereof is administered intravenously to the patient at a dose of about 3 µg/kg.

In an embodiment, the fusion protein of SEQ ID NO: 1 or variant thereof is administered to the patient daily for five consecutive days.

In an embodiment, the fusion protein of SEQ ID NO: 1 or variant thereof is administered to the patient at a dose of about 0.3 mg, about 0.6 mg, about 1 mg, about 3 mg, or about 10 mg. In an embodiment, the fusion protein of SEQ ID NO: 1 or variant thereof is administered subcutaneously to the patient at a dose of about 0.3 mg, about 0.6 mg, about 1 mg, about 3 mg, or about 10 mg.

In an embodiment, the fusion protein of SEQ ID NO: 1 or variant thereof is administered to the patient once every week, once every two weeks, or once every three weeks.

In an embodiment, the pembrolizumab is administered to the patient at a dose of 200 mg. In an embodiment, the pembrolizumab is administered intravenously to the patient at a dose of 200 mg. In an embodiment, the pembrolizumab is administered to the patient once every three weeks.

In an embodiment, the fusion protein of SEQ ID NO: 1 or variant thereof is administered intravenously to the patient at a dose of about 3 µg/kg daily for five consecutive days, every three weeks, and wherein the pembrolizumab is administered intravenously to the patient at a dose of about 200 mg once every three weeks.

In an embodiment, the fusion protein of SEQ ID NO: 1 or variant thereof is administered subcutaneously to the patient at a dose of about 0.3 mg once every week and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 0.3 mg once every week for 6 weeks prior to administration of the pembrolizumab.

In an embodiment, the fusion protein of SEQ ID NO: 1 or variant thereof is administered subcutaneously to the patient at a dose of about 0.6 mg once every week and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 0.6 mg once every week for 6 weeks prior to administration of the pembrolizumab.

In an embodiment, the fusion protein of SEQ ID NO: 1 or variant thereof is administered subcutaneously to the patient at a dose of about 1 mg once every week and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 1 mg once every week for 6 weeks prior to administration of the pembrolizumab.

In an embodiment, the fusion protein of SEQ ID NO: 1 or variant thereof is administered subcutaneously to the patient at a dose of about 3 mg once every week and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 3 mg once every week for 6 weeks prior to administration of the pembrolizumab.

In an embodiment, the fusion protein of SEQ ID NO: 1 or variant thereof is administered subcutaneously to the patient at a dose of about 1 mg once every three weeks and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 1 mg once every three weeks for 6 weeks prior to administration of the pembrolizumab.

In an embodiment, the fusion protein of SEQ ID NO: 1 or variant thereof is administered subcutaneously to the patient at a dose of about 3 mg once every three weeks and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 3 mg once every three weeks for 6 weeks prior to administration of the pembrolizumab.

In an embodiment, the fusion protein of SEQ ID NO: 1 or variant thereof is administered subcutaneously to the patient at a dose of about 10 mg once every three weeks and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 10 mg once every three weeks for 6 weeks prior to administration of the pembrolizumab.

In an embodiment, the patient failed to achieve complete remission (CR) following prior immune checkpoint inhibitor therapy.

In an embodiment, the patient has stable disease (SD), or partial response (PR) with no further reduction in tumor size or response, following prior immune checkpoint inhibitor therapy.

In an embodiment, the prior immune checkpoint inhibitor therapy comprises one or more of anti-PD-1 therapy, anti-PD-L1 therapy, and anti-CTLA-4 therapy.

In an embodiment, the method results in one or more of the following outcomes for the patient: increased duration of response (DOR); increased progression-free survival (PFS); increased time to progression (TTP); and increased overall survival (OS), relative to patients receiving the fusion protein of SEQ ID NO: 1 or the immune checkpoint inhibitor as a monotherapy, In an embodiment, the cancer is selected from the group consisting of squamous cell carcinoma of the head and neck, ovarian cancer, colorectal cancer, melanoma, and breast cancer.

BRIEF DESCRIPTION OF THE DRAWINGS

FIGS. 1A and 1B show diagrams of structural models of the fusion protein of SEQ ID NO: 1 (FIG. 1A) and its selective binding intermediate-affinity IL-2 receptor (FIG. 1B). The structural models in FIGS. 1A and 1B were generated using the experimentally determined crystal structure of the quaternary complex of human IL-2 bound to the trimeric high-affinity receptor (Wang et al., *Science.* 2005; 310(5751):1159-1163. doi: 10.1126/science.1117893).

FIGS. 4A-4C depict immunofluorescent staining for markers of lymphocyte tumor infiltration pre- and post-administration of the fusion protein of SEQ ID NO: 1. In FIG. 4A, CD3 and CD8 were stained alternative colors and the overlay between CD3 and CD8 was observed. In FIG. 4B, CD8 and granzyme B were stained alternative colors and the overlay between CD8 and granzyme B was observed. In FIG. 4C, PD-L1 and the tumor marker were stained alternative colors and the overlay was observed. A tumor marker stain was used to delineate the tumor cells in each panel.

FIGS. 9A and 9B graphically depicts mean tumor volume (FIG. 9A) and survival (FIG. 9B) in EMT-6 breast tumor model mice receiving: the fusion protein of SEQ ID NO: 2 in combination with an anti-CTLA-4 antibody; the fusion protein of SEQ ID NO: 2 alone; the anti-CTLA-4 antibody alone; or a vehicle control.

DETAILED DESCRIPTION OF THE INVENTION

Definitions

Figure 2:
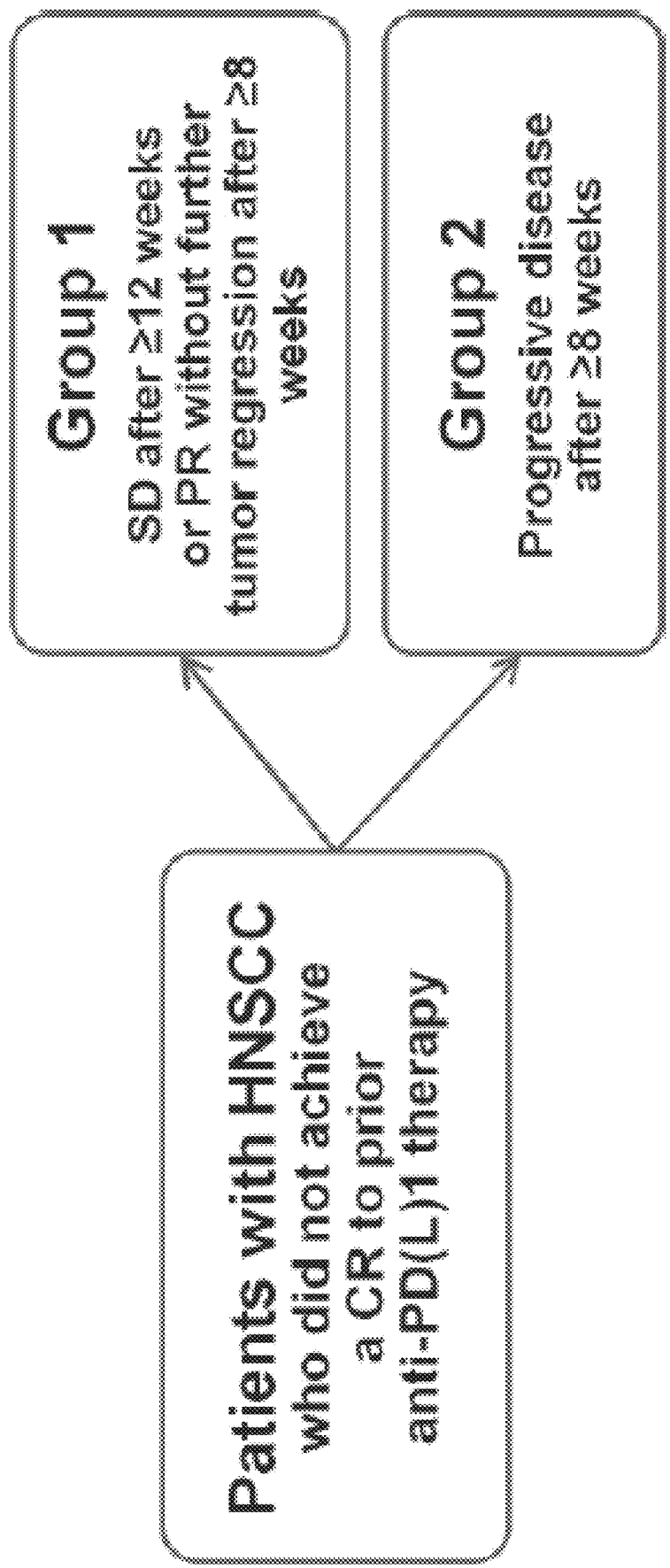
FIG. 2 is a study design schematic of the study described in Example 1. For the pembrolizumab regimen: 200 mg once Q3W by IV infusion. For the fusion protein of SEQ ID NO: 1 regimen: 3 μg/kg, given daily on 5 consecutive days on Days 1 through 5 of the first week of each 3-week treatment cycle. Abbreviations: CR=complete response; HNSCC=squamous cell carcinoma of the head and neck; PD-(L)1=programmed cell death ligand-1; PR=partial response; SD=stable disease; Q3W=every 3 weeks.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

As used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent. It is also noted that the term "comprising" is intended to be open and permits but does not require the inclusion of additional elements or steps. When the term "comprising" is used herein, the term "consisting of" is thus also encompassed and disclosed.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt. % to about 5 wt. %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The term "protein" or "peptide" as used herein refers to at least two or more amino acid residues linked together by peptide bond. The amino acid sequence in a protein or peptide is shown in the standard format, i.e., from amino terminus (N-terminus) to carboxyl terminus (C-terminus).

The term "fusion protein" designates a protein or peptide linked together with another protein or peptide by peptide bond between their respective N- and C-terminal amino acid residues or verse visa, or by insertion of the first protein or peptide into the internal region of the second protein or peptide by two peptide bonds at the N- and C-termini of the inserted protein or peptide. A peptide bond is a covalent chemical bond formed between carboxyl group of one amino acid and the amine group of another amino acid. A fusion protein is produced by expression of the fusion protein gene in an expression host, in which the coding sequence for the first protein or peptide is linked to the coding sequence of the second protein or peptide.

The invention also contemplates the use of a "variant" of the fusion protein of SEQ ID NO: 1 having an amino acid sequence having sequence identity that is about 75%, 80%, 85%, 90%, 91%, 92%, 93%, 94%, 95%, 96%, 97%, 98%, 99% or higher over a contiguous stretch of about 20 amino acids up to the full length of the fusion protein of SEQ ID NO: 1. A variant of the fusion protein of SEQ ID NO: 1 may have a defined sequence identity as compared to the fusion protein of SEQ ID NO: 1 over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

The "fusion protein of SEQ ID NO: 1" is also referred to herein as "cpIL-2:IL-2Rα" and is described in PCT application publication number, WO 2013/184942. The fusion protein of SEQ ID NO: 1 is a circularly permuted (cp) IL-2 variant fused to the extracellular domain of the IL-2Rα portion of the IL-2 receptor and has the following amino acid sequence:

(SEQ ID NO: 1)
SKNFHLRPRDLISNINVIVLELKGSETTFMCEYADETATIVEFLNRWITF

SQSIISTLTGGSSSTKKTQLQLEHLLLDLQMILNGINNYKNPKLTRMLTF

KFYMPKKATELKHLQCLEEELKPLEEVLNLAQGSGGGSELCDDDPPEIPH

ATFKAMAYKEGTMLNCECKRGFRRIKSGSLYMLCTGNSSHSSWDNQCQCT

SSATRNTTKQVTPQPEEQKERKTTEMQSPMQPVDQASLPGHCREPPPWEN

EATERIYHFVVGQMVYYQCVQGYRALHRGPAESVCKMTHGKTRWTQPQLI

CTG.

The invention also contemplates the use of a variant of the fusion protein of SEQ ID NO: 1 having an amino acid sequence having sequence identity that is about 75%, 80%, 85%, 90%, 91%, 92%, 93%, 94%, 95%, 96%, 97%, 98%, 99% or higher over a contiguous stretch of about 20 amino acids up to the full length of the fusion protein of SEQ ID NO: 1. A variant of the fusion protein of SEQ ID NO: 1 may have a defined sequence identity as compared to the fusion protein of SEQ ID NO: 1 over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a variant of the fusion protein of SEQ ID NO: 1 can comprise an amino acid sequence having at least about 75%, at least about 80%, at least about 85%, at least about 90%, at least about 95%, at least about 98%, or at least about 99%, amino acid sequence identity to a contiguous stretch of the fusion protein of SEQ ID NO: 1 from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length of the fusion protein of SEQ ID NO: 1.

The "fusion protein of SEQ ID NO: 2" is also referred to herein as "murine cpIL-2:IL-2Rα" and is described in U.S. Ser. No. 16/897,920. The fusion protein of SEQ ID NO: 2 is the murine ortholog of the fusion protein of SEQ ID NO: 1 and has the following amino acid sequence:

```
                                            (SEQ ID NO: 2)
SKSFQLEDAENFISNIRVTVVKLKGSDNTFECQFDDESATVVDFLRRWIA

FCQSIISTSPQGGSSSTQQQQQHLEQLLMDLQELLSRMENYRNLKLPRML

TFKFYLPKQATELKDLQCLEDELGPLRHVLDLTQGSGGGSELCLYDPPEV

PNATFKALSYKNGTILNCECKRGFRRLKELVYMRCLGNSWSSNCQCTSNS

HDKSRKQVTAQLEHQKEQQTTTDMQKPTQSMHQENLTGHCREPPPWKHED

SKRIYHFVEGQSVHYECIPGYKALQRGPAISICKMKCGKTGWTQPQLTCV

DGSHHHHHH.
```

The His-tag at the C-terminal end of the fusion protein of SEQ ID NO: 2 is used for purification and may be present in the expressed protein or optionally may be removed.

The term "IL-2 therapy" includes administration of immunotherapy based on IL-2 and its associated biological functions as an immunotherapy including but not limited to maintenance of CD4$^+$ regulatory T cells and differentiation of CD4$^+$ T cells into a variety of subsets; promotion of CD8$^+$ T-cell and NK cell cytotoxicity activity, and modulation of T-cell differentiation programs in response to antigen, promoting naive CD4$^+$ T-cell differentiation into T helper-1 (Th1) and T helper-2 (Th2) cells while inhibiting T helper-17 (Th17) differentiation. Therefore "IL-2 therapy" as used herein includes but is not limited to immunotherapy with rhIL-2 or a variant of rhIL-2 such as the fusion protein of SEQ ID NO: 1.

The terms "high dose IL-2" and "HD IL-2" include a dose of interleukin-2 (IL-2) of about or at least about 600,000 International Units (IU)/kg of body weight (kg)/dose, or about or at least about 720,000 IU/kg/dose.

The terms "low dose IL-2" and "LD IL-2" include a dose of interleukin-2 (IL-2) of less than about 600,000 IU/kg of body weight/dose, such as about 60,000 or about 72,000 IU/kg/dose, e.g., from about 60,000 to about 72,000 IU/kg/dose.

As used herein, the term "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants. Preferably "patient" refers to a human subject who may seek or be in need of treatment, requires treatment, is receiving treatment, will receive treatment, or a subject who is under care by a trained professional for a particular disease or condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable excipient" refers to a diluent, adjuvant, excipient or carrier with which a compound of the disclosure is administered. A pharmaceutically acceptable excipient is generally a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include water, any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The term "recombinant DNA technique" refers to the techniques for manipulating and combining two or more DNA sequences together that include recombination, PCR (polymerase chain reaction), in vitro mutagenesis, and direct DNA synthesis. These techniques are described in numerous published books and manuals, including the "Current protocols in molecular biology" (Ausubel eds. 2008. John Wiley & Son).

As used herein any form of administration or co-administration of a "combination", "combined therapy" and/or "combined treatment regimen" refers to at least two therapeutically active drugs or compositions which may be administered or co-administered, simultaneously, in either separate or combined formulations, or sequentially at different times separated by minutes, hours or days, but in some way act together to provide the desired therapeutic response.

As used herein, the term "parenteral" refers to dosage forms that are intended for administration as an injection or infusion and includes subcutaneous, intravenous, intra-arterial, intraperitoneal, intracardiac, intrathecal, and intramuscular injection, as well as infusion injections usually by the intravenous route.

The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. Preferably, an additional therapeutic agent is an anti-inflammatory agent.

The term "chemotherapeutic agent" refers to a compound or a derivative thereof that can interact with a cancer cell, thereby reducing the proliferative status of the cell and/or killing the cell for example, by impairing cell division or DNA synthesis, or by damaging DNA, effectively targeting fast dividing cells. Examples of chemotherapeutic agents include, but are not limited to, alkylating agents (e.g., cyclophosphamide, ifosfamide); metabolic antagonists (e.g., methotrexate (MTX), 5-fluorouracil or derivatives thereof); a substituted nucleotide; a substituted nucleoside; DNA demethylating agents (also known as antimetabolites; e.g., azacitidine); antitumor antibiotics (e.g., mitomycin, adriamycin); plant-derived antitumor agents (e.g., vincristine, vindesine, TAXOL®, paclitaxel, abraxane); cisplatin; carboplatin; etoposide; and the like. Such agents may further include, but are not limited to, the anti-cancer agents trimethotrexate (TMTX); temozolomide; raltitrexed; S-(4-Nitrobenzyl)-6-thioinosine (NBMPR); 6-benzyguanidine (6-BG); a nitrosoureas a nitrosourea (rabinopyranosyl-N-methyl-N-nitrosourea (Aranose), Carmustine (BCNU, BiCNU), Chlorozotocin, Ethylnitrosourea (ENU), Fotemustine, Lomustine (CCNU), Nimustine, N-Nitroso-N-methylurea (NMU), Ranimustine (MCNU), Semustine, Streptozocin (Streptozotocin)); cytarabine; and camptothecin; or a therapeutic derivative of any thereof.

The terms "treating" or "treatment" of a disease (or a condition or a disorder) as used herein refer to preventing the disease from occurring in a human subject or an animal subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and causing regression of the disease. With regard to cancer, these terms also mean that the life expectancy of an individual affected with a cancer may be increased or that one or more of the symptoms of the disease will be reduced. With regard to cancer, "treating" also includes enhancing or prolonging an anti-tumor response in a subject.

The phrase "therapeutically effective amount" or an "effective amount refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used. In reference to cancer or pathologies related to unregulated cell division, a therapeutically effective amount refers to that amount which has the effect of (1) reducing the size of a tumor (i.e., tumor regression), (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer. An "effective amount" is also that amount that results in desirable PD and PK profiles and desirable immune cell profiling upon administration of the therapeutically active compositions of the invention.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The term RECIST stands for Response Evaluation Criteria In Solid Tumors is a set of rules established and published by a collaboration of international authorities (e.g. European Organization for Research and Treatment of Cancer (EORTC), National Cancer Institute (NCI) of the U.S. and National Cancer Institute of Canada) that define when cancer patients improve ("respond"), stay the same ("stable") or worsen ("progression) during treatments.

The term iRECIST is a set of rules published by international authorities that better provide assessment of the effect of immunotherapeutic agents.

"Progression free survival (PFS)," as used in the context of the cancers described herein, refers to the length of time during and after treatment of the cancer until objective tumor progression or death of the patient. The treatment may be assessed by objective or subjective parameters; including the results of a physical examination, neurological examination, or psychiatric evaluation. In preferred aspects, PFS may be assessed by blinded imaging central review and may further optionally be confirmed by ORR or by blinded independent central review (BICR).

"Overall survival (OS)" may be assessed by OS rate at certain time points (e.g., 1 year and 2 years) by the Kaplan-Meier method and corresponding 95% CI will be derived based on Greenwood formula by study treatment for each tumor type. OS rate is defined as the proportion of participants who are alive at the time point. OS for a participant is defined as the time from the first dosing date to the date of death due to any cause.

As used herein a "complete response" (CR) is the disappearance of all signs of cancer in response to treatment. Complete response may also be referred to herein as "total remission" or a "complete remission".

As used herein the term "partial response" means a decrease in the size of the tumor, or in the extent of cancer in the body in response to treatment. Partial response may also be referred to herein as a "partial remission".

The term "cancer", as used herein, shall be given its ordinary meaning, as a general term for diseases in which abnormal cells divide without control.

The term "reducing a tumor" or "tumor regression" as used herein refers to a reduction in the size or volume of a tumor mass, a decrease in the number of metastasized tumors in a subject, a decrease in the proliferative status (the degree to which the cancer cells are multiplying) of the cancer cells, and the like.

The term "enhancing", as used herein, refers to allowing a subject or tumor cell to improve its ability to respond to a treatment disclosed herein. For example, an enhanced response may comprise an increase in responsiveness of at least 5%, 10%, 15%, 20%, 25%, 30%, 35%, 40%, 45%, 50%, 55%, 60%, 65%, 70%, 75%, 80%, 85%, 90%, 95% or 98% or more. As used herein, "enhancing" can also refer to enhancing the number of subjects who respond to a treatment such as a combination therapy comprising chemotherapy, drug-resistant immunocompetent cells, and immune checkpoint inhibitors. For example, an enhanced response may refer to a total percentage of subjects who respond to a treatment wherein the percentage is of at least 5%, 10%, 15%, 20%, 25%, 30%, 35%, 40%, 45%, 50%, 55%, 60%, 65%, 70%, 75%, 80%, 85%, 90%, 95% or 98% or more.

"Immune checkpoint proteins" regulate T cell function in the immune system. T cells play a central role in cell-mediated immunity. Checkpoint proteins interact with specific ligands that send a signal into the T cell and essentially switch off or inhibit T cell function. Cancer cells take advantage of this system by driving high levels of expression of checkpoint proteins on their surface that results in control of the T cells expressing checkpoint proteins on the surface of T cells that enter the tumor microenvironment, thus suppressing the anticancer immune response. As such, inhibition of immune checkpoint proteins by agents referred to herein as "(immune) checkpoint inhibitors" or "checkpoint inhibitors" would result in restoration of T cell function and an immune response to the cancer cells. Examples of checkpoint proteins include, but are not limited to: CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, OX40, B-7 family ligands or a combination thereof. Preferably, the immune checkpoint inhibitor interacts with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, OX40, A2aR, B-7 family ligands or a combination thereof.

The Fusion Protein of SEQ ID NO: 1

A recombinant human IL-2 variant fusion protein, described in WO 2013/184942, is a circularly permuted (cp) IL-2 variant fused to the extracellular domain of the IL-2Rα portion of the IL-2 receptor (FIG. 1) and is referred to herein as the "fusion protein of SEQ ID NO: 1" or has the following amino acid sequence:

```
                                            (SEQ ID NO: 1)
SKNFHLRPRDLISNINVIVLELKGSETTFMCEYADETATIVEFLNRWITF

SQSIISTLTGGSSTKKTQLQLEHLLLDLQMILNGINNYKNPKLTRMLTF

KFYMPKKATELKHLQCLEEELKPLEEVLNLAQGSGGGSELCDDDPPEIPH

ATFKAMAYKEGTMLNCECKRGFRRIKSGSLYMLCTGNSSHSSWDNQCQCT

SSATRNTTKQVTPQPEEQKERKTTEMQSPMQPVDQASLPGHCREPPPWEN

EATERIYHFVVGQMVYYQCVQGYRALHRGPAESVCKMTHGKTRWTQPQLI

CTG.
```

It is contemplated that fusion proteins that are closely related to the fusion protein of SEQ ID NO: 1, such as those fusion proteins having sequence identities of about 80%, 85%, 90%, 91%, 92%, 93%, 94%, 95%, 96%, 97%, 98%, 99% or higher identity over a contiguous sequence of at least about 20 amino acids up to the full length of the fusion protein of SEQ ID NO: 1 may also be suitable for administration in accordance with the methods of the invention.

The fusion protein of SEQ ID NO: 1 (FIG. 1A) is designed to selectively bind to and activate the intermediate-affinity IL-2R (FIG. 1B), but not the high-affinity IL-2R (FIG. 1B). The IL-2Rα domain of the fusion protein of SEQ ID NO: 1 serves to sterically impede the binding of the fusion protein of SEQ ID NO: 1 to the high-affinity IL-2R yet still allow binding to the intermediate-affinity IL-2R.

In vitro and in vivo nonclinical pharmacodynamic (PD) data support selective signaling through the intermediate-affinity IL-2 receptor by the fusion protein of SEQ ID NO: 1, leading to the activation and expansion of effector cells such as NK cells and CD8+ cells, while minimizing the activation and expansion of immunosuppressive $T_{regs}$. Additionally, in vivo in mice, the mouse surrogate of fusion protein of SEQ ID NO: 1 displays improved tolerability relative to rhIL-2 at doses that elicit equivalent or greater expansion of effector cells (e.g. NK cells and CD8+ cells) relative to $T_{regs}$.

First in human clinical data described in copending U.S. Patent Application Ser. No. 62/860,182 indicates that the fusion protein of SEQ ID NO: 1 activates expansion of CD8+ cells and NK cells in a dose dependent manner in the with minimal, non-dose dependent activation of Tregs. Therefore, the fusion protein of SEQ ID NO: 1 can be dosed in human patients at a concentration that is comparative to high dose rhIL-2 (e.g. aldesleukin) elicit equivalent or greater expansion of NK cells and CD8+ cells as compared to, for example, high dose rhIL-2 but with far less (at least two-fold less) relative expansion of immunosuppressive Tregs as compared to high dose rhIL-2 (Table 2).

Combination Therapy with Immune Checkpoint Inhibitors

Recurrent and metastatic diseases including but not limited to cancers comprising solid tumors for example, squamous cell carcinoma of the head and neck (HNCC), renal cell carcinoma (RCC), hepatic cell carcinoma (HCC), non-small cell lung cancer (NBCLC), and small cell lung cancer (SCLC), are often refractory or unable to be treated with further surgery and/or radiation therapy. The 5-year survival rate for later-stage diseases in many types of cancers is estimated to be 50% or less. Metastatic and recurrent HNSCC, for example, that is no longer amenable to local surgical/radiation therapy is associated with a high mortality rate and a median survival of 6 to 9 months. First-line therapy with platinum-based therapy in combination with 5FU and cetuximab offers some palliation and efficacy but also high treatment-related toxicity. For patients with disease progression after first-line therapy, or who are platinum intolerant or platinum refractory, the anti-programmed cell death protein-1 (PD-1) antibodies, nivolumab and pembrolizumab, have demonstrated substantial palliative benefits with durable tumor regressions noted.

Pembrolizumab is indicated for the treatment of patients with recurrent or metastatic solid tumors with disease progression on or after platinum-containing chemotherapy, and this therapy is considered standard of care. Pembrolizumab was granted accelerated approval in 2017 based on an overall response rate (ORR) of 16% (95% confidence interval [CI]: 11, 22) and a complete response rate of 5% in a non-randomized study of 174 patients with recurrent or metastatic HNSCC refractory to platinum-containing chemotherapy. Patients received pembrolizumab 10 mg/kg every 2 weeks (Q2W; n=53) or the now standard regimen of 200 mg every 3 weeks (Q3W; n=121) (Keytruda USPI). Among the 28 responding patients, the median duration of response (DOR) had not been reached (range 2.4+ to 27.7+ months), and the ORR and DOR were similar irrespective of dosage regimen (10 mg/kg Q2W or 200 mg Q3W) or human papillomavirus (HPV) status (Keytruda USPI). Subsequently, the efficacy of pembrolizumab was demonstrated in a single-arm study of 177 platinum- and cetuximab-pretreated HNSCC patients who had an ORR of 16% (95% CI:

11, 23) with a median DOR of 8 months (range 2+ to 12+ months. The open-label randomized Phase 3 study, Keynote 040, in platinum-pretreated HNSCC patients demonstrated that pembrolizumab narrowly failed to improve the primary endpoint of overall survival (OS) compared to the Investigator's choice therapy; the study's ORR was 14.6% in the pembrolizumab arm vs 10.1% with the active comparator (hazard ratio 0.81, one-sided P=0.0204. Adverse reactions occurring in patients with HNSCC were generally similar to those occurring in patients with melanoma or non-small cell lung cancer (NSCLC), with the exception of increased incidences of facial edema (10% all Grades; 2.1% Grades 3 to 4) and new or worsening hypothyroidism (14.6%).

The fusion protein of SEQ ID NO: 1 is an engineered fusion protein composed of a circularly permuted interleukin (IL)-2 and IL-2 receptor (R; IL-2R)-α designed to selectively activate the intermediate-affinity IL-2R, but not the high-affinity IL-2R. The intermediate-affinity IL-2R is expressed predominantly on effector lymphocytes, which play an important role in driving antitumor immune responses. In contrast, IL-2 (e.g. recombinant human IL-1) preferentially activates the high-affinity IL-2R, driving the expansion of high-affinity IL-2R-expressing cell types, including immunosuppressive CD4$^+$ regulatory T cells (T$_{regs}$), which limit anticancer activity by recombinant human IL-2 (aldesleukin).

The fusion protein of SEQ ID NO: 1 is agonist for IL-2Rβ and the common gamma chains, the two chains that make up the intermediate-affinity IL-2R. This is the same receptor complex stimulated by IL-15:IL-15Rα. Accordingly, the fusion protein of SEQ ID NO: 1 functions in a fashion similar to IL-15, in that it activates and expands CD8$^+$ T cell and natural killer (NK) cells in preference to other categories of T cells and lymphocytes. In early clinical data, both the fusion protein of SEQ ID NO; 1 and IL-15 function as T-cell growth factors that both activate and induce expansion of T cells and NK cells. PD-1 blocking antibodies "unleash" T cells, including T cells that can recognize and kill tumor cells. Theoretically, the combination of a T-cell growth factor with an agent that "unleashes" T cells should be synergistic in patients with T cells capable of recognizing and killing cancer cells. It is believed cancer patients previously treated with immune checkpoint inhibitors such as anti-PD-1 therapy (e.g., pembrolizumab or nivolumab) who have failed to achieve complete remission (CR) can achieve partial or complete tumor response by the addition of the fusion protein of SEQ ID NO: 1 in combination with an anti-PD-1 antibody therapy (e.g., pembrolizumab or nivolumab).

Therefore, the invention provides methods for combination treatment regimens for treating cancer in a patient in need thereof. The methods of the invention comprise: i) administering to the patient a therapeutically effective amount of a fusion protein of SEQ ID NO: 1; and ii) administering to the patient a therapeutically effective amount of an immune checkpoint inhibitor; wherein step (i) is carried out before, after or simultaneously with, step (ii).

The invention also provides combination treatment regimens for treating cancer in a patient comprising: i) administering to the patient a therapeutically effective amount of variant of the fusion protein of SEQ ID NO: 1 wherein the variant has an amino acid sequence that is about 80%, 85%, 90%, 91%, 92%, 93%, 94%, 95%, 96%, 97%, 98%, or 99% identical to the fusion protein of SEQ ID NO: 1 over a contiguous sequence of about 20 amino acids up to the full length the fusion protein of SEQ ID NO: 1; and ii) administering to the patient a therapeutically effective amount of an immune checkpoint inhibitor; wherein step (i) carried out before, after or simultaneously with step (ii).

With respect to administering steps (i) and (ii), these administering steps can be performed in either order (as well as simultaneously) and the invention is not limited in this regard. The administering step (i) may be carried out before administering step (ii). The administering step (ii) may be carried out before administering step (i). Both administering steps (i) and (ii) may be carried out simultaneously. Administering steps (i) and/or (ii) may be carried out repeatedly. Administering steps (i) and (ii) may be carried out only once.

Preferably, the combination therapy of the invention is for treating cancer in a patient who failed to achieve complete remission or partial remission to a prior treatment or an ongoing treatment using an immune checkpoint inhibitor alone or in combination with other complementary anti-cancer therapeutics as described herein. As used herein, a patient who fails to achieve complete or partial remission to treatment with an immune checkpoint inhibitor relates to a subject who fails to achieve complete remission or partial remission according to the RECIST (Response Evaluation Criteria In Solid Tumors) criteria or according to the irRECIST (immune-related Response Evaluation Criteria In Solid Tumors) criteria. Preferably, the patient has failed to achieve complete remission to a prior or ongoing treatment using an immune checkpoint inhibitor alone or in combination with a complementary anti-cancer therapeutic.

Preferably the combination therapy of the invention treats cancer in a subject in which monotherapy with an immune checkpoint protein inhibitor or monotherapy with the fusion protein of SEQ ID NO: 1 cannot achieve complete remission or partial remission in the patient.

Preferably, the combination therapy of the invention provides complete remission of cancer in the patient in a shorter time frame than that achieved using treatment with an immune checkpoint inhibitor alone or with the fusion protein of SEQ ID NO: 1 alone.

Preferably, an effective amount of the fusion protein of SEQ ID NO: 1 or variant thereof is an amount effective to, for example, cause a dose dependent increase in circulating NK cells and CD8+ cells in a patient with minimal, non-dose-dependent increase in circulating T regulatory (Treg) cells. Preferably, the increase in circulating NK cells and CD8+ cells relative to the increase in circulating T regulatory (Treg) is greater in a patient administered the fusion protein of SEQ ID NO: 1.

One skilled in the art can determine an effective amount using standard assays such as the FACS analysis of cells or tissue treated with the fusion protein of SEQ ID NO: 1 as a monotherapy or in a combination therapy with an immune checkpoint inhibitor as described herein in the Examples.

In general, dosing parameters of monotherapy with the fusion protein of SEQ ID NO: 1 or any of the combination therapies described herein dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

In addition, an effective dose of the fusion protein of SEQ ID NO: 1 can be an amount that, when administered in one or more doses to a subject, produces a desired result relative to a healthy subject. For example, for a subject experiencing a particular disorder, an effective dose can be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The invention provides dosages contained in a "unit dosage form". The phrase "unit dosage form" refers to physically discrete units, each unit containing a predetermined amount of the fusion protein of SEQ ID NO: 1 either alone or in combination with one or more immune checkpoint inhibitors and optionally one or more additional therapeutic agents sufficient to produce the desired effect. It will be appreciated that the parameters of a unit dosage form will depend on the particular agent and the effect to be achieved.

Preferably an effective amount of the fusion protein of SEQ ID NO: 1 that is an amount administered to a patient encompassed by one or more of the following ranges: from about 0.01 to 1 mg/kg; from about 0.01 mg/kg to about 0.1 mg/kg; from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

Preferably, the invention provides pharmaceutical compositions for subcutaneous administration comprising a fixed dose of the fusion protein of SEQ ID NO: 1 of at least about 0.3 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, or 30 mg of the fusion protein of SEQ ID NO: 1. The pharmaceutical compositions of the invention may optionally include a pharmaceutically acceptable excipient.

Preferably, the invention provides pharmaceutical compositions for subcutaneous administration comprising a dose of the fusion protein of SEQ ID NO: 1 in terms of mg/kg as is often necessary for pediatric patients, for example, the invention provides the fusion protein of SEQ ID NO: 1, at a dose of about 0.1 µg/kg, 0.3 µg/kg, 1 µg/kg, 3 µg/kg, 3.5 µg/kg, 4 µg/kg, 4.5 µg/kg, 5 µg/kg, 5.5 µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg 14.5 µg/kg or a corresponding fixed dose thereof based on an about 12 to about 50 kg or more child or a 60-70 kg adult.

An effective amount of the fusion protein of SEQ ID NO: 1 in combination with an immune checkpoint inhibitor may not be the same as an effective amount of the fusion protein of SEQ ID NO: 1 when delivered as a monotherapy. However, so long as the combined treatment regimen provides the desired results, the amount of the fusion protein of SEQ ID NO: 1 used in the combined treatment regimen is deemed to be therapeutically effective. Preferably, the amount of an immune checkpoint inhibitor that is normally administered as a monotherapy is less when used in combination with the fusion protein of SEQ ID NO: 1.

The combination treatment regimen including the fusion protein of SEQ ID NO: 1 may include administration of a single daily dose of the fusion protein of SEQ ID NO: 1 over a series of consecutive or non-consecutive days. For example, SEQ ID NO: 1 may be administered on Days 1-5 of treatment with a rest period of 1 day to 28 days, while the immune checkpoint inhibitor may be administered on day 1 of treatment and administered once every 21 days (i.e., once every three weeks) after that for as long as treatment lasts.

The actual dose and frequency of administration of the fusion protein of SEQ ID NO: 1 in combination with an immune checkpoint inhibitor protein will vary depend upon the age, weight, and general condition of the subject as well as the severity of the condition being treated, the judgment of the health care professional, and conjugate being administered. The dosing and frequency may also be established based on whether the patient is responsive to one or more of the compounds in the combination. For example, patients may be responsive to the individual agents alone as well as the combination but are more responsive to the combination. By way of further example, patients may be non-responsive to one of the individual agents but are responsive to the combination. By way of still further example, patients may be non-responsive to either of the individual agents alone but are responsive to the combination.

The combination therapy methods described herein include administering at least one immune checkpoint inhibitor in combination with the fusion protein of SEQ ID NO: 1. The invention is not limited to any specific immune checkpoint inhibitor so long as the immune checkpoint inhibitor inhibits one or more activities of the target checkpoint proteins when administered in an effective amount as monotherapy or in combination with the fusion protein of SEQ ID NO: 1. In some instances, due to, for example, synergistic effects, minimal inhibition of the immune checkpoint protein by the immune checkpoint inhibitor may be sufficient in the presence of the fusion protein of SEQ ID NO: 1. Many immune checkpoint inhibitors are known in the art, for example, the following is a list of FDA approved immune checkpoint inhibitors:

ipilimumab (YERVOY®)
pembrolizumab (KEYTRUDA®)
atezolizumab (TECENTRIQ®)
durvalumab (IMFINZ®)
avelumab (BAVENCIO®)
nivolumab (OPDIVO®)
cemiplimab (LIBTAYO®).

Additional examples of anti-PD-1 antibodies in the clinic include, but are not limited to, sintilimab (TYVYT®), toripalimab (JS001), camrelizumab (AiRuiKa™), tislelizumab (BGB-A317), spartalizumab (PDR001), retifanlimab (MGA012), balstilimab (AGEN2034), cetrelimab (JNJ-63723283), dostarlimab (TSR-042), and sasanlimab (PF-06801591).

Examples of immune checkpoint proteins (ligands and receptors), some of which are selectively upregulated in various types of tumor cells, that are candidates for blockade include PD1, PDL1, BTLA, CTLA4, TIM3, LAG3; A2aR; and Killer Inhibitory Receptors.

CTLA4 (cytotoxic T-lymphocyte associated antigen 4; also known as CD152). The immune checkpoint receptor CTLA4 belongs to the immunoglobulin superfamily of receptors, which also includes PD1; BTLA; lymphocyte attenuator; TIM3, and V-domain immunoglobulin suppressor of T cell activation. CD80 (also known as B7.1) and CD86 (also known as B7.2) have been identified as the CTLA4 receptor ligands. CTLA4, the first immune checkpoint receptor to be clinically targeted, is expressed exclusively on T cells, where it primarily regulates the amplitude of the early stages of T cell activation. It has been shown to counteract the activity of the T cell co-stimulatory receptor CD28. Upon antigen recognition, CD28 signaling strongly amplifies T-cell receptor signaling to activate T cells. [See, e.g., Riley et al., (2002) Proc. Natl Acad. Sci. USA 99:11790-95]. CTLA4 is transcriptionally induced following T cell activation. Although CTLA4 is expressed by activated CD8+ effector T cells, its primary physiological role is believed to be manifested through distinct effects on the two major subsets of CD4+ T cells: i) down-modulation of helper T cell activity, and ii) enhancement of regulatory T cell immunosuppressive activity. Specifically, CTLA4 blockade results in immune response enhancement dependent on helper T cells, while CTLA4 engagement of regulatory T cells increases their suppressive function. [See, e.g., Fontenot et al., (2003) Nat. Immunol. Proc. 4:330-36].

Various experimental approaches have been described targeting the CTLA4 signaling pathway using anti-CTLA4 antagonistic antibodies. These approaches have been evaluated to discern the potential utility of such antibodies in cancer (e.g., tumor) and infectious conditions. For example, IL-10 has previously been implicated in CTLA4-mediated suppression of anti-tumor immune responses (Jovasevic et al., (2004) J. Immunol. 172:1449-54). When it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Another agent, tremelimumab (formerly ticilimumab; MedImmune) is currently in clinical trials for, for example, hepatocellular carcinoma, melanoma and mesothelioma.

The CD28 signaling pathway has also been targeted using antagonistic CTLA4-Ig for potential utility in autoimmune and transplantation conditions (Wu et al., (2012) Int. J. Biol. Sci. 8:1420-30). Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus.

PD1 (programmed cell death protein 1; also known as CD279), and PDL1 (PD1 ligand; also known as B7-H1) and PDL2. PD1 is a negative regulator of T cell activation that shares structural properties with members of the CD28 family. PD1 limits T cell effector functions within tissues. By up-regulating ligands for PD1, tumor cells block antitumor immune responses in the tumor microenvironment. As with many other immune checkpoint inhibitors, PD1 blockade reverses T cell exhaustion, restores cytokine production, and augments the expansion of antigen-dependent T cells. PDL1 and PDL2 are the two ligands known to activate the PD1 pathway. Blockade of the PD1-PDL1/PDL2 pathway has been shown to delay tumor growth and prolong the survival of tumor-bearing mice. In addition, the results of early-stage clinical trials suggested that blockade of the PD1 pathway induced sustained tumor regression in a variety of tumor types. For PD1 and PDL1/PDL2, the most important interaction is believed to be at the tumor site, rather than more broadly across the immune system as it is with CTLA-4.

Various immunotherapeutic approaches that modulate the PD1-PDL1/PDL2 pathway using gene transfer and/or antagonistic antibodies have been evaluated. Such approaches have shown promise in a number of diseases, disorders and conditions, including transplantation, infection, tumor, and autoimmune disease (Wu et al., (2012) Int. J. Biol. Sci. 8:1420-30). The extracellular immunoglobulin (Ig) V domain of PD1 has been shown to be important for the interaction between PD1 and PDL1/PDL2, suggesting that hPD1-IgV can be a promising strategy for specific tumor immunotherapy (Zhang et al., (2008) Cytotherapy 10(7):711-10). PD1 antibodies are under development (e.g., nivolumab (Bristol-Myers Squibb), pidilizumab (CT-011; CureTech) and lambrolizumab (Merck)). Nivolumab has shown promise in patients with melanoma, lung and kidney cancer. Combination therapy comprising nivolumab and the CTLA-4 modulator ipilimumab is also being evaluated in lung cancer. Anti-PDL1 antibodies are also being evaluated (e.g., BMS-936559 (Bristol-Myers Squibb), MPDL3280A (Genentech/Roche) and MEDI4736 (MedImmune), as are anti-PDL2 antibodies (e.g., AMP-224 (Amplimmune/GlaxoSmithKline)).

Preferably, the immune checkpoint inhibitor is a biologic therapeutic or a small molecule. Preferably, the immune checkpoint inhibitor is a monoclonal antibody, a humanized antibody, a fully human antibody, a fusion protein or a combination thereof.

The skilled person may refer to the literature to obtain information on identifying and testing the activity of any potential immune checkpoint inhibitor and also determining suitable dosage and frequency with which to administer the immune checkpoint inhibitor alone or in combination with SEQ ID NO: 1. The amount of immune checkpoint inhibitor administered that is sufficient to promote checkpoint protein inhibition is referred to herein as an "checkpoint protein-inhibitory amount" or dosage range. The skilled person may refer to the scientific literature and package insert of commercially available inhibitors to establish checkpoint-inhibitory amounts for use in the combination therapy of the invention.

Preferably, an effective amount of an immune checkpoint inhibitor is that amount effective to cause tumor regression in combination with the fusion protein of SEQ ID NO: 1. Preferably, the immune checkpoint inhibitor is administered (in terms of kg of patient body weight) in less than 0.0001 mg/kg, 0.0001-0.001 mg/kg, 0.001-0.01 mg/kg, 0.01-0.05 mg/kg, 0.05-0.1 mg/kg, 0.1-0.2 mg/kg, 0.2-0.3 mg/kg, 0.3-0.5 mg/kg, 0.5-0.7 mg/kg, 0.7-1 mg/kg, 1-2 mg/kg, 2-3 mg/kg, 3-4 mg/kg, 4-5 mg/kg, 5-6 mg/kg, 6-7 mg/kg, 7-8 mg/kg, 8-9 mg/kg, 9-10 mg/kg, at least 10 mg/kg, or any combination thereof doses. Preferably, the immune checkpoint inhibitor is administered at least once a week, at least twice a week, at least three times a week, at least once every two weeks, or at least once every month or multiple months. Preferably, the immune checkpoint inhibitor is administered as a single dose, in two doses, in three doses, in four doses, in five doses, or in 6 or more doses.

Preferably, the immune checkpoint inhibitor is a PD1 immune checkpoint inhibitor comprising one or more anti-PD-1 antibodies, including nivolumab and pembrolizumab. A preferred treatment regimen of the invention combines the fusion protein of SEQ ID NO: 1 with the immune checkpoint inhibitor, pembrolizumab. Preferably 200 mg of pembrolizumab is administered in accordance with manufacturer's recommendations, generally once every three weeks or 21 days.

Preferably, the immune checkpoint inhibitor is a CTLA4 immune checkpoint inhibitor comprising one or more anti-CTLA-4 antibodies, including ipilimumab. A preferred treatment regimen of the invention combines the fusion protein of SEQ ID NO: 1 with the immune checkpoint inhibitor, ipilimumab. Preferably 200 mg of ipilimumab is administered in accordance with manufacturer's recommendations, generally once every three weeks or 21 days.

Generally, a therapeutically effective amount of the fusion protein of SEQ ID NO: 1 when combined with an immune checkpoint inhibitor is an amount sufficient to activate the cytotoxicity of CD8+ T cells, to reduce or eliminate the tumor. Preferably the combination therapy of the invention results in a complete response to treatment in at least about 50%, about 60%, about 70%, about 80% and about 90% or more of the patient population tested with the combination therapy and preferably the complete response is a durable complete response.

Preferably, the fusion protein of SEQ ID NO: 1 is administered in a combination treatment of cancer by intravenous or subcutaneous injection and preferably the immune checkpoint inhibitor is administered by intravenous or subcutaneous injection. However, other modes of administration of both compounds are also contemplated, such as pulmonary, nasal, buccal, rectal, sublingual and transdermal. As used herein, the term "parenteral" refers to dosage forms that are intended for administration as an injection or infusion and includes subcutaneous, intravenous, intra-arterial, intraperitoneal, intracardiac, intrathecal, and intramuscular injection, as well as infusion injections usually by the intravenous route. Each pharmacological component of the method can be administered separately. Alternatively, if administration of two pharmacological components is desired to be simultaneous, and the two pharmacological components are compatible together and in a given formulation, then the simultaneous administration can be achieved via administration of single dosage form/formulation (e.g., intravenous administration of an intravenous formulation that contains both pharmacologically active agents). One of ordinary skill in the art can determine through routing testing whether two given pharmacological components are compatible together and in a given formulation.

The compositions administered in accordance with the invention may further comprise with a pharmaceutically acceptable diluent, carrier, solubilizer, emulsifier, preservative and/or adjuvant and another pharmaceutical composition comprising one or more therapeutic agents, such as a therapeutic antibody, with a pharmaceutically acceptable diluent, carrier, solubilizer, emulsifier, preservative and/or adjuvant.

The combination treatment methods described herein can continue for as long as the clinician overseeing the patient's care deems the treatment method is effective. Non-limiting parameters that indicate the treatment method is effective include the following: tumor shrinkage (in terms of weight and/or volume); a decrease in the number of individual tumor colonies; tumor elimination; and progression-free survival (PFS).

Exemplary lengths of time associated with the course of combination therapy disclosed herein include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years.

Preferably the fusion protein of SEQ ID NO: 1 and pharmaceutical compositions thereof, in combination with one or more immune checkpoint inhibitors to treat and/or prevent various diseases, disorders and conditions (e.g., cancers) is affected by utilizing particular dosing parameters that serve to minimize any adverse effects associated with administration of the individual therapies by themselves. By way of example, the addition of the fusion protein of SEQ ID NO: 1 regimen to a regimen comprising an immune checkpoint inhibitor (e.g. ipilimumab) might allow a reduction of the amount of immune checkpoint inhibitor needed to achieve the therapeutic goal, thus reducing (or even eliminating) severe and fatal immune-mediated adverse reactions that prompted the FDA to require a "black box" warning on certain immune checkpoint inhibitors (e.g. ipilimumab).

Treatment Indications

The combination treatment methods described herein are particularly suitable for the treatment of cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Examples of the solid tumor cancers that may be treated using the combination treatment regimens described herein include, but are not limited to: pancreatic cancer, colorectal cancer, non-small cell lung cancer, renal cell carcinoma; squamous cell carcinoma of the head and neck, bladder cancer, cancers of the prostate, cervix, stomach, endometrium, brain, liver, ovary, testis, head, neck, skin (including melanoma and basal carcinoma), mesothelial lining, esophagus, breast, muscle, connective tissue, lung (including small-cell lung carcinoma and non-small-cell carcinoma), adrenal gland, thyroid, kidney, or bone; glioblastoma, mesothelioma, gastric cancer, sarcoma, choriocarcinoma, cutaneous basocellular carcinoma, and testicular seminoma. In preferred aspects, the cancer is cervical cancer, non-small cell lung cancer, renal cell carcinoma; squamous cell carcinoma of the head and neck, bladder cancer, pancreatic cancer, melanoma, lymphoma or gastric cancer. In more preferred aspects, the cancer is melanoma, non-small cell lung cancer, squamous cell carcinoma of the head and neck, bladder cancer, renal cell carcinoma or gastric carcinoma. The treatment regimens of the invention are particularly suited for treating solid tumors including but not limited to: lymphomas, melanoma, renal cell carcinoma (RCC), advanced solid tumors, tumors that have previously been treated with therapeutic therapy but remain refractory to previous therapies.

Cancers that may also be treated in accordance with invention include, but are not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Glioblastoma, Childhood; Glioblastoma, Adult; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Neurofibroma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland' Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor, among others.

The treatment regimens of the invention are particularly suited for treating solid tumors including but not limited to: lymphomas, melanoma, renal cell carcinoma (RCC), hepatic cell carcinoma (HCC), non-small cell lung cancer (NBCLC), small cell lung cancer (SCLC), squamous cell carcinoma of the head and neck (SCCHN) and including advanced solid tumors and tumors that have previously been treated with anti-cancer therapy but remain refractory to previous therapies.

Pharmaceutical Compositions

The fusion protein of SEQ ID NO: 1 and immune checkpoint inhibitors of the present disclosure can be in the form of one or more compositions suitable for administration to a subject. In general, such compositions are "pharmaceutical compositions" comprising the fusion protein of SEQ ID NO: 1 and/or an immune checkpoint inhibitor(s), and one or more pharmaceutically acceptable or physiologically acceptable diluents, carriers or excipients.

The pharmaceutical compositions of the invention can be formulated to be compatible with the intended method or route of administration; exemplary routes of administration are set forth herein. Furthermore, the pharmaceutical compositions can be used in combination with other therapeutically active agents or compounds as described herein in order to treat or prevent the diseases, disorders and conditions as contemplated by the present disclosure.

The pharmaceutical compositions typically comprise a therapeutically effective amount of the fusion protein of SEQ ID NO: 1 and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form.

Preferably, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver IL-10, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oleagenous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butane diol. Acceptable diluents, solvents and dispersion media that can be employed include water, Ringer's solution, isotonic sodium chloride solution, CREMOPHOR EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions can be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions can also be in the form of oil-in-water emulsions. The oily phase can be a vegetable oil, for example olive oil or arachis oil, or a mineral oil, for example, liquid paraffin, or mixtures of these. Suitable emulsifying agents can be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

Suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The pharmaceutical compositions suitable for use in accordance with the invention may be in any format (e.g., sprays for nasal or inhalation use) currently known or developed in the future.

The concentration of a fusion protein of SEQ ID NO: 1 or an immune checkpoint inhibitor in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Complementary Combination Therapy/Additional Therapeutic Agents

Other anticancer treatment regimens in further combination with the combination therapy of the fusion protein of SEQ ID NO: 1 and an immune checkpoint inhibitor are also contemplated for use as further combination therapy for the treatment of cancer. Other anticancer treatment regimens include other therapeutic immunotherapies such as adoptive cell transfer regimens, antigen-specific vaccination, inhibition of DNA repair proteins (e.g. inhibitors of the nucleic enzyme poly(adenosine 5'-diphospho-ribose) polymerase ["poly(ADP-ribose) polymerase" PARP inhibitors"]) and combinations with more than one immune checkpoint inhibitor molecule.

The methods of the invention may be further combined with other therapeutic agents and/or anti-cancer agents. Preferably, the therapeutic agent and/or anti-cancer agent is an antibody. Preferably, the therapeutic agent is a therapeutic protein. Preferably, the therapeutic agent is a small molecule. Preferably the anticancer agent is an antigen. Preferably, the therapeutic agent is a population of cells. Preferably, the therapeutic agent is a therapeutic antibody. Preferably the therapeutic agent is another cytotoxic and/or chemotherapeutic agent. The term "cytotoxic agent" as used herein refers to a substance that inhibits or prevents a cellular function and/or causes cell death or destruction. Chemotherapeutic agent includes chemical compounds useful in the treatment of cancer.

In any such additional combination therapy, the various additional therapeutic agent(s) frequently have different mechanisms of action than the fusion protein of SEQ ID NO: 1 and/or the immune checkpoint inhibitor(s). Such additional combination therapy can be especially advantageous by allowing a further dose reduction of one or more of the agents, thereby reducing or eliminating the adverse effects associated with one or more of the agents; furthermore, such additional combination therapy can have a synergistic therapeutic or prophylactic effect on the underlying disease, disorder, or condition.

Preferably each of the fusion protein of SEQ ID NO: 1, the immune checkpoint inhibitor(s) and the additional therapeutic agent(s) can be in a separate dosage forms or in combined dosage forms. Preferably, the fusion protein of SEQ ID NO: 1, the immune checkpoint inhibitor(s) and the supplemental agent(s) (e.g., a chemotherapeutic agent) are administered or applied sequentially. However, one or more of the therapeutic agents may be administered simultaneously while one or more are administered sequentially. Regardless of whether the fusion protein of SEQ ID NO: 1, the immune checkpoint inhibitor(s) and the additional therapeutic agent(s) are administered sequentially, simultaneously, or some variation thereof, they are considered to be administered as supplementary combination therapy for purposes of the present disclosure.

Any possible dosing regimen for the additional combination therapy that may be acceptable, appropriate or optimal under the circumstances is preferred. The regimens described hereafter are exemplary, not exclusionary. Preferably, treatment with the fusion protein of SEQ ID NO: 1, the immune checkpoint inhibitor(s), and the additional therapeutic agent(s) are maintained over a period of time. Preferably, treatment with the fusion protein of SEQ ID NO: 1, the immune checkpoint inhibitor(s), and the additional therapeutic agent(s) are reduced or continued over a period to time (e.g., when the subject is stable). Preferably, treatment with the additional therapeutic agent(s) is reduced or discontinued (e.g., when the subject is stable), while treatment with the fusion protein of SEQ ID NO: 1 and the immune checkpoint inhibitor(s) is maintained at a constant dosing regimen. Preferably, treatment with the supplemental agent(s) is reduced or discontinued (e.g., when the subject is stable), treatment with the fusion protein of SEQ ID NO: 1 is reduced (e.g., lower dose, less frequent dosing or shorter treatment regimen), and treatment with the immune checkpoint inhibitor is maintained at a constant dosing regimen. Preferably, treatment with the additional therapeutic agent(s) is reduced or discontinued (e.g., when the subject is stable), treatment with fusion protein of SEQ ID NO: 1 is reduced (e.g., lower dose, less frequent dosing or shorter treatment regimen), and treatment with the immune checkpoint inhibitor(s) is maintained at a constant dosing regimen. Preferably, treatment with the additional therapeutic agent(s) and the fusion protein of SEQ ID NO: 1 is maintained at a constant dosing regimen, while treatment with the immune checkpoint inhibitor(s) is reduced or discontinued (e.g., when the subject is stable). Preferably, treatment with the additional therapeutic agent(s) and the immune checkpoint inhibitor(s) is maintained at a constant dosing regimen, while treatment with the fusion protein of SEQ ID NO: 1 is reduced or discontinued (e.g., lower dose, less frequent dosing or shorter treatment regimen). Identification and use of other dosing regimens will be apparent to the skilled artisan.

The present invention provides the use of additional therapeutic agents (e.g., chemotherapeutic agents) for treating and/or preventing cancer, tumor, or precancerous or cancer-associated disease, disorder or condition. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. Preferably, combination therapy comprises administration of a hormone or related hormonal agent.

Any other agent useful in the treatment or prevention of the cancerous conditions described herein is contemplated as a supplementary agent, including, but not limited to, a cytokine such as IL-2 or cytokine antagonist, such as IL-12, INFα, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

Recombinant Production

Preferably the fusion protein of SEQ ID NO: 1 is produced using recombinant techniques. The fusion protein can be produced as an intracellular protein or as a secreted protein, using any suitable construct and any suitable host cell, which can be a prokaryotic or eukaryotic cell, such as a bacterial (e.g., $E.\ coli$) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al., (1995) Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The fusion protein of SEQ ID NO: 1 can be prepared in substantially pure or isolated form (e.g., free from other polypeptides). The polypeptides can be present in a composition that is enriched for the polypeptide relative to other components that can be present (e.g., other polypeptides or other host cell components). For example, purified fusion protein can be provided such that the fusion protein is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

Preferably, the fusion protein of SEQ ID NO: 1 may be produced using a biological recombinant expression system typically involving transfecting cells with a DNA vector that contains a genetic template encoding the fusion protein of SEQ ID NO: 1 and then culturing the cells so that they transcribe and translate the Fusion Protein. Typically, the cells are then lysed to extract the expressed protein for subsequent purification. Both prokaryotic and eukaryotic in vivo protein expression systems are suitable for use. Preferably, the fusion protein of SEQ ID NO: 1 is produced in CHO cells.

Kits

Also provided are kits comprising a fusion protein of SEQ ID NO: 1 formulated for administration, and optionally any other chemotherapeutic or anti-cancer agent. The kits are generally in the form of a physical structure housing various components, as described below, and can be utilized, for example, in practicing the methods described above. A kit can include the fusion protein of SEQ ID NO: 1 (provided in, e.g., a sterile container), which can be in the form of a pharmaceutical composition suitable for administration to a subject.

The pharmaceutical composition can be provided in a form that is ready for use or in a form requiring, for example, reconstitution or dilution prior to administration. When the compositions are in a form that needs to be reconstituted by a user, the kit can also include buffers, pharmaceutically acceptable excipients, and the like, packaged with or separately from the fusion protein of SEQ ID NO: 1. When combination therapy (e.g., the fusion protein of SEQ ID NO: 1 and an immune checkpoint inhibitor(s) is contemplated, the kit can contain the several agents separately or they can already be combined in the kit. Similarly, when additional complementary therapy is required (e.g., a fusion protein of SEQ ID NO: 1, an immune checkpoint inhibitor(s), and an additional complementary therapy or agent), the kit can contain the several agents separately or two or more of them can already be combined in the kit.

A kit of the invention can be designed for conditions necessary to properly maintain the components housed therein (e.g., refrigeration or freezing). A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.).

Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

EXAMPLES

The following examples are offered by way of illustration and are not to be construed as limiting the invention as claimed in any way.

Example 1—Study Design ION Study

TABLE 2

List of Abbreviations and Definition of Terms

| Abbreviation or Term | Full Form of Definition |
|---|---|
| ACTH | Adrenocorticotropic hormone |
| ADA | Anti-drug antibody |
| AE | Adverse event |
| ALK-P | Alkaline phosphatase |
| ALT | Alanine aminotransferase |
| ANC | Absolute neutrophil count |
| aPTT | Activated partial thromboplastin time |
| AST | Aspartate aminotransferase |
| BCG | Bacillus Calmette-Guérin |
| BUN | Blood urea nitrogen |
| C | Cycle |
| CBC | Complete blood count |
| CI | Confidence interval |
| CIML | Central Immune Monitoring Laboratory |
| CNS | Central nervous system |
| $CO_2$ | Carbon dioxide |
| CR | Complete response/remission |
| CrCl | Creatinine clearance |
| CRO | Contract research organization |
| CSA | Clinical Study Agreement |
| CT | Computerized tomography |
| CTCAE | Common Terminology Criteria for Adverse Events |
| D | Day |

TABLE 2-continued

List of Abbreviations and Definition of Terms

| Abbreviation or Term | Full Form of Definition |
|---|---|
| DKA | Diabetic ketoacidosis |
| DLT | Dose-limiting toxicities |
| DNA | Deoxyribonucleic acid |
| DOR | Duration of response |
| D/C | Discontinuation |
| ECG | Electrocardiogram |
| ECI | Events of clinical interest |
| ECOG | Eastern Cooperative Oncology Group |
| eCRF | Electronic case report form |
| EDC | Electronic data capture |
| ELISA | Enzyme-linked immunosorbent assay |
| EOT | End of Treatment |
| FDG | Fluorodeoxyglucose |
| FHCRC | Fred Hutchinson Cancer Research Center |
| FIH | First-in-human |
| FNA | Fine needle aspiration |
| FU | Follow-up |
| GCP | Good Clinical Practice |
| GFR | Glomerular filtration rate |
| GI | Gastrointestinal |
| GMP | Good Manufacturing Practice |
| HBsAg | Hepatitis B surface antigen |
| hCG | Human chorionic gonadotropin |
| HCV | Hepatitis C virus |
| HIV | Human immunodeficiency virus |
| HNSCC | Squamous cell carcinoma of the head and neck |
| HPV | Human papillomavirus |
| hsTCRB | Human T-cell receptor beta chain |
| IB | Investigator's Brochure |
| ICF | Informed consent form |
| ICH | International Council on Harmonisation |
| ID | Identification |
| IEC | Independent ethics committee |
| IFN | Interferon |
| IHC | Immunohistochemistry |
| IL | Interleukin |
| IL-2R | Interleukin-2 receptor |
| INR | International normalized ratio |
| ION | Immune Oncology Network |
| irAE | Immune-related adverse event |
| IRB | Institutional review board |
| irRC | Immune-related response criteria |
| IUD | Intrauterine device |
| IV | Intravenous, intravenously |
| Kyn | Kynurenine |
| LDH | Lactic dehydrogenase |
| MedDRA | Medical Dictionary for Regulatory Activities |
| MFI | Mean fluorescence intensity |
| MRI | Magnetic resonance imaging |
| NCCN | National Comprehensive Cancer Network |
| NCI | National Cancer Institute |
| NK | Natural killer |
| NSAID | Nonsteroidal anti-inflammatory drug |
| NSCLC | Non-small cell lung cancer |
| ORR | Overall response rate |
| OS | Overall survival |
| PBMC | Peripheral blood mononuclear cell |
| PCR | Polymerase chain reaction |
| PD | Progressive disease |
| PD-1 | Programmed cell death protein-1 |
| PD-L1 | Programmed cell death ligand-1 |
| PET | Positron emission tomography |
| PFS | Progression-free survival |
| PI | Principal Investigator |
| PR | Partial response/remission |
| PT | Prothrombin time |
| Q2W | Every 2 weeks |
| Q3W | Every 3 weeks |
| R | Receptor |
| RECIST | Response Evaluation Criteria in Solid Tumors |
| RNA | Ribonucleic acid |
| rRNA | Ribosomal ribonucleic acid |
| SAE | Serious adverse event |
| SAP | Statistical Analysis Plan |
| SD | Stable disease |

TABLE 2-continued

List of Abbreviations and Definition of Terms

| Abbreviation or Term | Full Form of Definition |
|---|---|
| SOP | Standard operating procedures |
| SRC | Safety Review Committee |
| T1DM | Type 1 diabetes mellitus |
| TB | Tuberculosis |
| TCR | T-cell receptor |
| TCRB | T-cell receptor beta chain |
| TEAE | Treatment-emergent adverse event |
| TIL | Tumor-infiltrating lymphocytes |
| TMB | Tumor mutational burden |
| TME | Tumor microenvironment |
| $T_{reg}$ | Regulatory T cell |
| Trp | Tryptophan |
| TSH | Thyroid-stimulating hormone |
| TTP | Time to progression |
| ULN | Upper limit of normal |
| US | United States |
| USP-NF | United States Pharmacopeia-National Formulary |
| WGS | Whole genome shotgun |
| WHO-ATC | World Health Organization-Anatomical Therapeutic Chemical (drug classification system) |

Summary

This phase 2 multi-site trial, clinical study, is designed to estimate the response rate to the fusion protein of SEQ ID NO: 1 in combination with the anti-PD-1 therapy KEYTRUDA® (pembrolizumab) in patients with advanced or recurrent head and neck squamous cell cancer who did not achieve complete response with an anti-PD-(L)1 antibody treatment. Secondary objectives include evaluation of the duration of response, progression-free survival, time to progression and overall survival of patients with advanced or recurrent head and neck squamous cell cancer receiving treatment with the fusion protein of SEQ ID NO: 1 in combination with pembrolizumab. As an exploratory objective, this clinical study will assess the tumor microenvironment using paired tumor biopsies to evaluate potential predictive biomarkers for response to the addition of the fusion protein of SEQ ID NO: 1.

Objectives

Primary

To estimate the response rate to the fusion protein of SEQ ID NO: 1 in combination with pembrolizumab in patients with squamous cell carcinoma of the head and neck (HNSCC) who have previously received anti-programmed cell death protein 1 (anti-PD-1) or anti-programmed cell death ligand-1 (anti-PD-L1) (henceforth referred to as PD-[L]1) therapy but who have not achieved a complete remission (CR). The primary objective will be assessed for the following 2 groups:

Group 1: Patients with stable disease (SD), defined as ≥12 weeks of SD per Response Evaluation Criteria in Solid Tumors (RECIST) v1.1 criteria, or patients with partial response (PR) with no further reduction in tumor size or response (i.e., PR and not improving further) for ≥8 weeks on prior anti-PD-(L)1 therapy;

Group 2: Patients with progressive disease (PD) with no prior response to anti-PD-(L)1 therapy after ≥8 weeks on anti-PD-1 therapy or patients currently with PD after prior achievement of a best response of SD or PR and after ≥8 weeks on anti-PD-(L)1 therapy.

Secondary

To evaluate the duration of response (DOR), progression-free survival (PFS), time to progression (TTP), and overall survival (OS) of patients with advanced or recurrent HNSCC receiving pembrolizumab plus the fusion protein of SEQ ID NO: 1;

To evaluate the safety and tolerability of pembrolizumab plus the fusion protein of SEQ ID NO: 1.

Exploratory

To evaluate whether assessment of pretreatment biopsies from patients who have failed to achieve a CR on therapy with anti-PD-(L)1 can identify a subset of patients who are likely to respond to the addition of the fusion protein of SEQ ID NO: 1;

To evaluate whether a second biopsy, timed during combined therapy, can identify changes in tumors that will predict response or failure to the addition of the fusion protein of SEQ ID NO: 1.

Methodology: This is a multi-center, Phase 2, open-label therapy study to assess the antitumor efficacy of SEQ ID NO: 1 in combination with pembrolizumab in patients with advanced, recurrent and/or metastatic HNSCC on treatment with an anti-PD-(L)1 antibody without having achieved a CR.

Investigational Product, Dosage, Duration, and Mode of Administration: Fusion protein of SEQ ID NO: 1 drug product is a sterile, white to off-white, lyophilized powder for IV infusion. Each single-use vial contains 2.28 mg to deliver 2 mg of the fusion protein of SEQ ID NO: 1. When reconstituted as directed, each mL contains 1 mg of the fusion protein of SEQ ID NO: 1 as a clear, colorless solution. The excipients included in the fusion protein of SEQ ID NO: 1 formulation are citric acid monohydrate, United States Pharmacopeia-National Formulary (USP-NF); sodium citrate tribasic dihydrate, USP-NF; sucrose, USP-NF; and polysorbate 20, USP-NF. Fusion protein of SEQ ID NO: 1 drug product must be stored and refrigerated at 2° C. to 8° C. (36° F. to 46° F.). Fusion protein of SEQ ID NO: 1 drug product is supplied with sterile water for injection, USP for reconstitution of the lyophilized material. Diluent containing polysorbate 20 is supplied separately for use. Reconstituted the fusion protein of SEQ ID NO: 1 is administered via a 30-minute IV infusion once daily for 5 consecutive days during the first week of each treatment cycle.

Fusion protein of SEQ ID NO: 1 should be administered by infusion beginning 60 to 90 minutes after the completion of pembrolizumab infusion. Pembrolizumab is to be administered as an IV infusion over 30 minutes in a dose of 200 mg Q3W, for up to 1 year for as long as patients are deriving clinical benefit (i.e., objective response or SD) and tolerating therapy well.

Duration of Study: This study consists of a 28-day screening period, treatment period, and 30-day post-treatment follow-up. The treatment period consists of at least five 3-week cycles that can repeat for up to 1 year screening.

Statistical Methods: For all applicable parameters, descriptive statistics will be provided.

Efficacy: Response to treatment will be evaluated using both Response Evaluation Criteria in Solid Tumors v1.1 (RECIST 1.1) and immune-related response criteria (Irecist). For patients with objectively measurable disease, response to therapy, DOR, PFS, and OS will be calculated.

Primary efficacy endpoint will be evaluated in the Efficacy Evaluable population (all patients who received at least 1 dose of both study drugs) for each group separately and overall. The rate of objective improvement after continued anti-PD-1 therapy with the fusion protein of SEQ ID NO: 1 will be summarized by groups (Group 1 and Group 2) and overall population with descriptive statistics. The analysis of objective response using an exact binomial test will be conducted separately for each group and overall; the 95% confidence interval will be reported.

Secondary efficacy endpoints will be evaluated in the Efficacy Evaluable population (Group 1 and Group 2).

DOR and TTP will be calculated and summarized by group and overall. PFS and OS curves will be plotted by group and overall using the Kaplan-Meier (KM) approach. The median survival time (if applicable) and its 95% CI for PFS and OS will be reported. The PFS and OS rates at 6 and 12 months will be estimated using the KM approach.

The objective response rate will be summarized for each of the 4 cohorts.

The percentage change from baseline in target lesions will be summarized by groups and overall.

Study Rational

Although the clinical studies with nivolumab and pembrolizumab have demonstrated antitumor activity and established the efficacy, activity, and benefits with anti-PD-1 therapy in the recurrent metastatic platinum-experienced HNSCC population, the response rates remain low, and the numbers of patients who relapse or fail to achieve CR remain in the high majority of 85% or more. As patients with HNSCC suffer tremendous morbidity and mortality with this disease, and the efficacy of any single-agent chemotherapy remains low with no proven salvage options in this population that fails anti PD-1 therapy, there is an exceptionally high unmet need to discover new therapies or effective combination immunotherapy to enhance, improve, or restore the responses to anti-PD-1 therapy.

This study will enroll patients who have received prior anti-PD-1 antibody therapy (pembrolizumab or nivolumab) as their last treatment or those receiving ongoing current anti-PD-1 antibody therapy who have not achieved a CR. Programmed cell death protein-1:programmed cell death ligand-1 (PD-L1) (henceforth referred to as PD-[L]1) inhibitors are effective in small subsets of virtually every histologic type of cancer, yet most treated patients fail to benefit. Moreover, many of the tumors that respond eventually relapse. Therefore, it is highly likely that, in the near future, patients with stable disease (SD) or progressing on anti-PD-(L)1 therapy will likely be the largest single category of patients in the US. In the long-term follow-up analysis of the KEYNOTE-012 study of single agent pembrolizumab conducted in 192 patients with HNSCC, the objective response rate was 18% (95% CI, 13% to 24%) (Mehra et al, 2018, Br. J. Cancer. 119(2):153-159). Among the subset of patients achieving a response, the median time to best response was 2 months (range, 2 to 17 months). Thus, after a period of 8 weeks on pembrolizumab monotherapy treatment, approximately 9% of the original population, or approximately 10% of the remaining population who have not yet responded, would be expected to experience a new response if pembrolizumab monotherapy were continued. If the fusion protein of SEQ ID NO: 1 can increase responses relative to monotherapy anti-PD-(L)1 response, this would support the further development of strategies using the combination of the fusion protein of SEQ ID NO: 1 plus immune checkpoint blockade as the first-line combination immunotherapy for HNSCC and other malignancies.

Discerning the character of the tumors in patients who are not achieving complete regression on PD-(L)1 inhibition with anti-PD1 or anti-PD-L is essential. Thus, pretreatment biopsies will be mandated. At present, the tumors most likely to respond to anti-PD-1 are those with an increased number of mutations and thus abnormal proteins containing potentially immunogenic epitopes and infiltration of T cells capable of recognizing the abnormal proteins. Mechanisms by which tumors fail to respond to anti-PD-1 are not yet comprehensively defined but include insufficient infiltrated CD8+ T cells, lack of PD-L1 induction by interferon (IFN)-γ secreted from infiltrating CD8+ T cells, lack of tumor response to cytotoxic molecules, failure of apoptosis, presence of suppressive cells and molecules in the tumor microenvironment (TME), and mechanical barriers mediated by vascular or stromal factors. There are likely to be many more redundant and non-redundant mechanisms of failure. Presumably, some mechanisms of failure will be rescued by the fusion protein of SEQ ID NO: 1 (e.g., recruitment of CD8+ T cells to the TME) and some will not).

While it is not currently possible to hypothesize the frequency or proportion of each mechanism, we believe that biopsies from participants prior to and during therapy will provide insight into purported mechanisms of failure or success to generate hypotheses that will provide the foundation for future study design.

Assessment of whether addition of the fusion protein of SEQ ID NO: 1 can induce remission for patients with tumors that do not respond to anti-PD-1 treatment is the essential goal of the study. Understanding whether the fusion protein of SEQ ID NO: 1 alters the number of NK cells and T cells within tumors is also critical. Thus, the post-treatment (second) biopsy will be collected during Week 2 (Cycle [C] 1, Day [D] 12 or at any time from C1D8 through C1D19).

The study population designates patients with advanced or recurrent HNSCC who are either refractory and progressive on prior anti-PD-(L)1 therapy or have failed to obtain response or tumor regression to anti-PD-1 therapy for more than 8 weeks to receive the fusion protein of SEQ ID NO: 1 in combination with pembrolizumab. Patients in this population are as follows:

Group 1 (Cohorts 1 and 2) will consist of all patients with current SD (for at least 12 weeks) or partial response (PR) with no further reduction in tumor size or response for ≥8 weeks (i.e., PR and not further improving).

Group 2 (Cohorts 3 and 4) will consist of patients with progressive disease (PD) with no prior response to anti-PD-(L)1 therapy after ≥8 weeks on anti-PD-(L)1 or current PD after prior achievement of a best response of SD or PR and after ≥8 weeks on anti-PD-(L)1 therapy.

HNSCC was chosen as an exemplary cancer due to the high unmet need in this difficult-to-treat patient population with no effective therapeutic options for a number of reasons: 1) the demonstrated efficacy and recent approval of pembrolizumab for previously platinum-experienced recurrent or metastatic HNSCC, 2) the ease of serial biopsies in easily accessible sites of tumor in a proportion of patients, and 3) the responses to the combination of the fusion protein of SEQ ID NO: 1 and pembrolizumab being readily and easily assessable. However, if efficacy or response is observed, the combination could be tested in many different cancers.

This study will be performed in collaboration with the Immune Oncology Network (ION), who will perform activities related to, but not limited to, oversight and management of clinical sites, medical monitoring, and laboratory analysis services.

Dose Selection

Pembrolizumab

The pembrolizumab dose of 200 mg Q3W is the approved dose for the treatment of patients with HNSCC (Keytruda USPI).

The Fusion Protein of SEQ ID NO: 1

All patients in this study will be given the fusion protein of SEQ ID NO: 1 at a daily dose of 3 µg/kg for 5 consecutive days on Days 1 through 5 of the first week of each 3-week treatment cycle.

A first-in-human (FIH) clinical study with the fusion protein of SEQ ID NO: 1 has been initiated and is currently ongoing. This study is being conducted in patients with advanced solid tumors who are refractory or intolerant to therapies known to provide clinical benefit. Patients are administered SEQ ID NO: 1 by a 30-minute intravenous (IV) infusion daily for 5 days followed by an off-treatment period in repeating cycles.

Dosing is repeated every 21 days, except during the first treatment cycle, which is 14 days. Interim data from study participants receiving 0.1 to 3.0 µg/kg/day the fusion protein of SEQ ID NO: 1 in the FIH study showed a dose-proportional increase in systemic exposure to the fusion protein of SEQ ID NO: 1 and a dose-dependent increase in circulating NK cells and $CD8^+$ T cells with minimal and non-dose-dependent effect on Tregs. At the 3 µg/kg dose level (n=8), one incident each of Grade 3 febrile neutropenia and Grade 3 hypoalbuminemia met the protocol definitions for dose-limiting toxicities (DLT). DLT definitions were subsequently amended to loosen DLT criteria and allow continued dose escalation.

The combination of expected pharmacodynamic effects and favorable tolerability of 3 µg/kg the fusion protein of SEQ ID NO: 1 supports the evaluation of this dose in combination therapy.

Overall Study Design and Plan

The study will assess the antitumor efficacy of the fusion protein of SEQ ID NO: 1 in combination with pembrolizumab in patients with advanced, recurrent, and/or HNSCC on treatment with an anti-PD-(L)1 antibody (pembrolizumab or nivolumab) without having achieved a CR.

The study is a multi-center, Phase 2, open-label therapy study in collaboration with ION. Patients must have received anti-PD-(L)1 therapy prior to enrollment into the study. After enrollment in the study, the fusion protein of SEQ ID NO: 1 with pembrolizumab will be administered to 4 cohorts of patients with advanced, recurrent, and/or metastatic HNSCC who have received anti-PD-(L)1 therapy whose current response is as follows:
Cohort 1: SD, defined as ≥12 weeks of SD per RECIST criteria;
Cohort 2: PR with no further reduction in tumor size or response for ≥8 weeks (i.e., PR and not improving further);
Cohort 3: PD with no prior response to anti-PD-(L)1 therapy after ≥8 weeks on anti-PD-(L)1, or
Cohort 4: Current PD after prior achievement of best response of SD or PR and after ≥8 weeks on anti-PD-(L)1 therapy.

Patients will be administered the combination of the fusion protein of SEQ ID NO: 1 and pembrolizumab. For simplification, the 4 cohorts of patients will be combined into 2 arms:
Group 1 will consist of all patients with current SD or PR (Cohorts 1 and 2) who are not progressing or further demonstrating reductions in tumor size.
Group 2 will consist of patients with PD (Cohorts 3 and 4).

Baseline tumor biopsy will be required at the time of study entry after screening procedures have been completed and prior to first administration of combination regimen to assess each patient's tumor characteristics in an effort to identify patients with tumors that may have limited pembrolizumab efficacy or potential response to an anti-PD-1/ fusion protein of SEQ ID NO: 1 combination. Tumors will be assessed for quantity and character of tumor-infiltrating T cells and other leukocytes, and for quantitative assessment of PD-L1 expression, gene signatures that correlate with response or lack of response and will be sequenced to determine the number of nonsynonymous gene mutations that might serve T-cell targets.

Patients will also have a post-treatment (second) biopsy at C1D12, or at any time from C1D8 through C1D19, to assess whether the addition of the fusion protein of SEQ ID NO: 1 to the treatment regimen alters the TME and what changes on therapy (immunopharmacodynamics) predispose to responses to the combination.

The study plans to enroll 19 and 12 evaluable patients for Groups 1 and 2, respectively. The number of patients enrolled into each cohort within each group will be determined at the time of enrollment, based on the patient's response to previous treatment There is a potential to expand a particular cohort of interest up to a maximum of 50 patients per group.

Pembrolizumab will be administered according to the standard regimen of 200 mg flat dose IV Q3W. Fusion protein of SEQ ID NO: 1 will be administered IV at a daily dose of 3 µg/kg, given daily on 5 consecutive days on Days 1 through 5 of the first week of each 3-week treatment cycle.

Fusion protein of SEQ ID NO: 1 may be continued until toxicity develops. If a toxicity attributed to the fusion protein of SEQ ID NO: 1 occurs, dosing for both pembrolizumab and the fusion protein of SEQ ID NO: 1 will be held. After recovery from an AE that meets dose hold criteria, the patient may resume at full dose of pembrolizumab and full or reduced dose of the fusion protein of SEQ ID NO: 1 in subsequent cycles with consultation from the Medical Monitor or may discontinue from the study. Pembrolizumab will be continued Q3W until termination criteria are confirmed; no dose modification of pembrolizumab will be allowed. Dose reduction of the fusion protein of SEQ ID NO: 1 from 3 µg/kg/day to 1 µg/kg/day may be allowed.

Patients with tumors who respond to treatment will continue until the following:
Confirmed progression occurs (upon agreement with the ION and Alkermes Medical Monitors, patients tolerating therapy and receiving clinical benefit may be allowed to stay on study for up to 1 year);
Until unacceptable toxicity occurs;
Other criteria for discontinuation occur.

Safety and tolerability will be assessed and reported using standard Common Terminology Criteria for Adverse Events (CTCAE) v5.0 criteria. Safety will be monitored by the study Principal Investigator (PI), participating site PIs, the ION Coordinating Center PI and staff, and representatives from Alkermes. Details pertaining to the Safety Review Committee (SRC), including participants, frequency of meetings, and criteria that would trigger ad hoc meetings, are described in the SRC Charter.

If the unacceptable AEs observed are typical of known pembrolizumab and/or the fusion protein of SEQ ID NO: 1 toxicities, the following will be considered: (1) revising the protocol eligibility requirements to decrease the likelihood of toxicities, (2) modifying the dose or schedule, or (3) allowing the study to proceed as designed assuming that patients in this study will have fatal diseases and few other treatment options. The risk/benefit ratio will need to be evaluated in this situation.

If unexpected, unacceptable AEs are considered to be related to concurrent administration of the fusion protein of SEQ ID NO: 1 and pembrolizumab, the PI, participating site PIs, the ION Coordinating Center PI and staff, and representatives from Alkermes will consider revising the protocol eligibility requirements to decrease the likelihood of toxicities or may consider allowing the study to proceed as designed given the risk/benefit ratio for this population.

Figure 3:
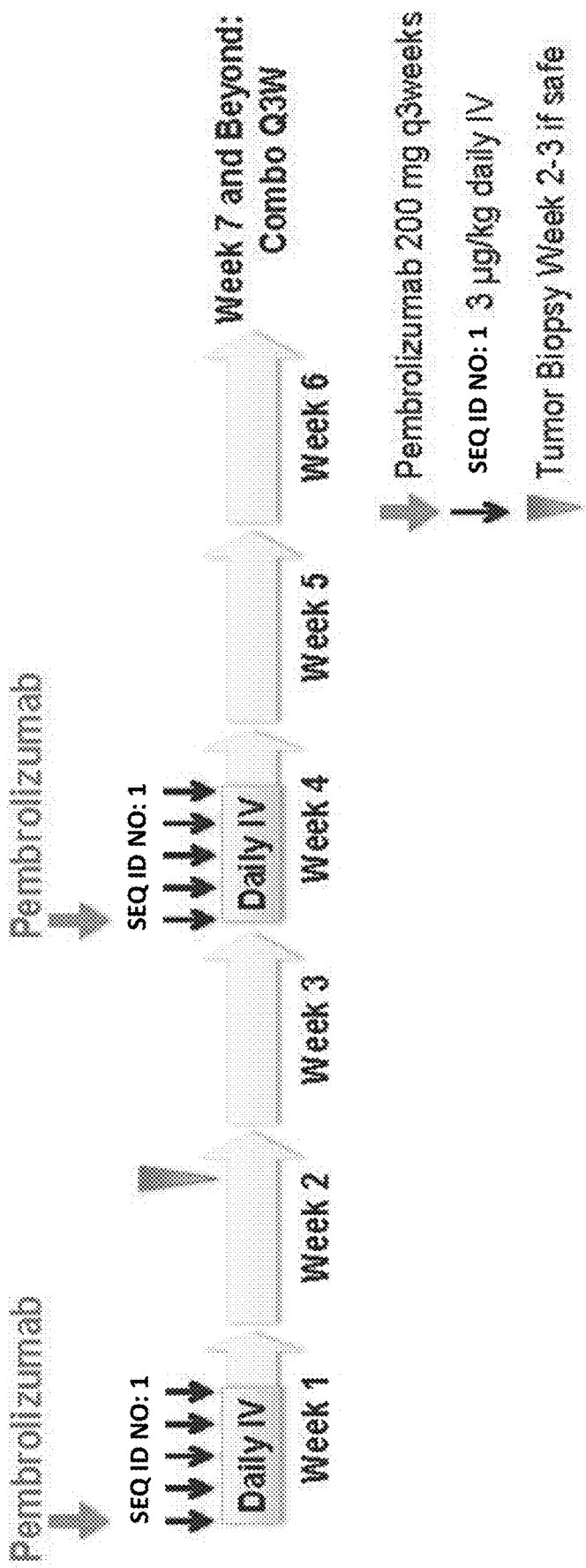
FIG. 3 is a study design schematic of the study described in Example 1. Abbreviations: IV=intravenous; Q3W=every 3 weeks.

Study design schematics are provided in FIG. 2 and FIG. 3.

Tumor Imaging and Assessment of Disease

For the purposes of this study, baseline scans must be done within 28 days before beginning treatment. In addition to a baseline scan, the first on-study imaging time point will be performed at 6 weeks (±7 days) after first dose, then within 7 days prior to every second cycle thereafter, or more frequently if clinically indicated while the patient is on study.

Patients whose response converts from PD or SD to PR or from PR to CR will have a confirmatory scan for tumor assessments 6 weeks after the response-defining scan. If the patient continues on study after confirmatory scan, then the patient would receive scan per regular schedule. Thereafter, timing of tumor assessments will depend on whether or not the patient continues with study drug.

Patients with an Investigator-determined confirmed CR according to RECIST v1.1 may be discontinued from study drug if they have 1) been treated for at least 24 weeks with pembrolizumab and SEQ ID NO: 1 before discontinuing therapy and 2) received at least 2 treatments with pembrolizumab and SEQ ID NO: 1 beyond the date when the initial CR was declared.

If radiologic imaging shows PD, tumor assessment may be repeated by the site approximately 4 to 6 weeks later in order to confirm PD with the option of continuing treatment, as described below, while awaiting radiologic confirmation of progression. If repeat imaging shows a reduction in the tumor burden compared to the initial scan demonstrating PD, treatment may be continued as per treatment calendar.

Accumulating evidence indicates that a minority of patients treated with immunotherapy may derive clinical benefit despite initial evidence of PD. Allowance to continue treatment despite initial radiologic progression takes into account the observation that some patients can have a transient tumor flare in the first few months after the start of immunotherapy but with subsequent disease response. Patients will be permitted to continue on treatment beyond initial RECIST v1.1-defined PD as long as they meet the following criteria:

Investigator-assessed clinical benefit and no rapid disease progression.

Patient continues to meet relevant eligibility criteria, as determined by the ION and Alkermes Medical Monitors (or designee) in discussion with the Investigator.

Stable performance status.

Patient is tolerating study treatment.

Treatment beyond progression will not delay an imminent intervention to prevent serious complications of disease progression (e.g., CNS metastases).

The decision to continue treatment beyond initial Investigator-assessed progression should be discussed with the ION and Alkermes Medical Monitors (or designee) and documented in the study records. A follow-up scan should be performed at the next scheduled imaging evaluation 6 weeks later to determine whether there has been a decrease in the tumor size or continued PD. The assessment of clinical benefit should be balanced by clinical judgment as to whether the patient is clinically deteriorating and unlikely to receive any benefit from continued treatment. If the Investigator feels that the patient continues to achieve clinical benefit by continuing treatment, then the patient should remain on the study and continue to receive monitoring according to the Schedule of Assessments.

In determining whether or not the tumor burden has increased or decreased, investigators should consider all target lesions as well as non-target lesions. The decision to continue study drug after the first evidence of disease progression determined by radiologic imaging is at the Investigator's discretion based on the clinical status of the patient as described in Table 1.

Patients may receive study drug while waiting for confirmation of PD if they are clinically stable as defined by the following criteria:

Absence of signs and symptoms (including worsening of laboratory values) indicating disease progression.

No decline in ECOG performance status.

Absence of rapid progression of disease.

Absence of progressive tumor at critical anatomical sites (e.g., cord compression) requiring urgent alternative medical intervention.

TABLE 1

| Disease assessment by RECISTv1.1 | Tumor Imaging/Assessment for Disease Progression | | | |
|---|---|---|---|---|
| | Clinically Stable | | Clinically Unstable | |
| | Imaging | Treatment | Imaging | Treatment |
| 1st radiologic evidence of | Repeat imaging at approximately 4 | May continue study drug at the | Repeat imaging at | Discontinue treatment if |

TABLE 1-continued

Tumor Imaging/Assessment for Disease Progression

| Disease assessment by RECISTv1.1 | Clinically Stable | | Clinically Unstable | |
|---|---|---|---|---|
| | Imaging | Treatment | Imaging | Treatment |
| PD | to 6 weeks to confirm PD | Investigator's discretion while awaiting confirmatory scan | approximately 4 to 6 weeks to confirm PD if possible | alternative therapy is warranted |
| Repeat scan confirms PD[a] | No additional imaging required | Discontinue treatment | No additional imaging required | NA |
| Repeat scan shows SD, PR, or CR | Continue regularly scheduled imaging assessments prior to every 3$^{rd}$ cycle[b] | Continue study drug at the Investigator's discretion | Continue regularly scheduled imaging assessments prior to every 3$^{rd}$ cycle[b] | May restart study drug if condition has improved and/or clinically stable per Investigator's discretion |

Abbreviations:
CR = complete remission;
NA = not applicable;
PD = progressive disease;
PR = partial response;
RECIST = Response Evaluation Criteria in Solid Tumors;
SD = stable disease.
[a]Patients who are otherwise clinically stable may be continued on study drug, per Investigator discretion. Even if the patient remains otherwise stable, study drug will be discontinued if tumor burden increases by 25% or more following initial confirmation of progression.
[b]Tumor imaging/assessment will be performed at baseline, at 9 weeks, and prior to every 3$^{rd}$ cycle.

Response and progression for purpose of publication will be evaluated in this study using the new international criteria proposed by the revised RECIST v1.1 guideline. Changes in the largest diameter (unidimensional measurement) of the tumor lesions and the shortest diameter in the case of malignant lymph nodes will be used in the RECIST criteria.

Often with immunotherapy, tumors appear larger before they decrease in size. This could be particularly relevant if the fusion protein of SEQ ID NO: 1 drives NK and CD8+ T cells into tumors. Clinicians are encouraged to consider this possibility to avoid stopping potentially effective immunotherapy too soon.

Definitions

Evaluable for toxicity: All patients will be evaluable for toxicity from the time of consent.

Evaluable for objective response: Only those patients who have measurable disease present at baseline, have received at least one cycle of therapy, and have had their disease re-evaluated will be considered evaluable for response. These patients will have their response classified according to the definitions stated below. (NOTE: Patients who exhibit objective disease progression prior to the end of Cycle 1 will also be considered evaluable.)

Evaluable Non-Target Disease Response: Patients who have lesions present at baseline that are evaluable but do not meet the definitions of measurable disease, have received at least one cycle of therapy, and have had their disease re-evaluated will be considered evaluable for non-target disease. The response assessment will be based on the presence, absence, or unequivocal progression of the lesions.

Disease Parameters

Measurable disease: For the purposes of this study, measurable lesions are defined according to RECIST v1.1 criteria. All tumor measurements must be recorded in mm (or decimal fractions of centimeters). NOTE: Tumor lesions that are situated in a previously irradiated area might or might not be considered measurable.

Malignant lymph nodes: To be considered pathologically enlarged and measurable, a lymph node must be ≥15 mm in short axis when assessed by computerized tomography (CT) scan (CT scan slice thickness recommended to be no greater than 5 mm). At baseline and in follow-up, only the short axis will be measured and followed.

Non-measurable disease: All other lesions (or sites of disease), including small lesions (longest diameter <10 mm or pathological lymph nodes with ≥10 to <15 mm short axis), are considered non-measurable disease. Bone lesions, leptomeningeal disease, ascites, pleural/pericardial effusions, lymphangitis cutis/pulmonis, inflammatory breast disease, and abdominal masses (not followed by CT or magnetic resonance imaging [MRI]), are considered as non-measurable.

NOTE: Cystic lesions that meet the criteria for radiographically defined simple cysts should not be considered as malignant lesions (neither measurable nor non-measurable) since they are, by definition, simple cysts. 'Cystic lesions' thought to represent cystic metastases can be considered as measurable lesions, if they meet the definition of measurability described above. However, if non-cystic lesions are present in the same patient, these are preferred for selection as target lesions.

Target lesions: All measurable lesions up to a maximum of 2 lesions per organ and 5 lesions in total, representative of all involved organs, should be identified as target lesions and recorded and measured at baseline. Target lesions should be selected on the basis of their size (lesions with the longest diameter), be representative of all involved organs, but in addition should be those that lend themselves to reproducible repeated measurements. It may be the case that, on occasion, the largest lesion does not lend itself to reproducible measurement; in such circumstance, the next largest lesion which can be measured reproducibly should be selected. A sum of the diameters (longest for non-nodal lesions, short axis for nodal lesions) for all target lesions will be calculated and reported as the baseline sum diameters. If lymph nodes are to be included in the sum, then only the short axis is added into the sum. The baseline sum diameters will be used as a reference to further characterize any objective tumor regression in the measurable dimension of the disease.

Non-target lesions: All other lesions (or sites of disease) including any measurable lesions over and above the 5 target lesions should be identified as non-target lesions and should also be recorded at baseline. Measurements of these lesions are not required, but the presence, absence, or rare cases of unequivocal progression of each should be noted throughout follow-up.

Methods for Evaluation of Measurable Disease

All measurements should be taken and recorded in metric notation using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up. Imaging-based evaluation is preferred to evaluation by clinical examination unless the lesion(s) being followed cannot be imaged and are only assessable by clinical examination. Methods allowable for disease evaluation are as follows:

Clinical examination: For skin lesions, documentation by color photography, including a ruler to estimate the size of the lesion, is recommended. Clinical lesions will only be considered measurable when they are superficial (e.g., skin nodules and palpable lymph nodes) and ≥10 mm diameter as assessed using calipers (e.g., skin nodules).

Chest x-ray: Lesions on chest x-ray are acceptable as measurable lesions when they are clearly defined and surrounded by aerated lung. However, CT is preferable.

Conventional CT and MRI: A CT scan may be used to measure the lesion if the CT slice thickness is 5 mm or less. If CT scans have slice thickness greater than 5 mm, the minimum size for a measurable lesion should be twice the slice thickness. MRI is also acceptable in certain situations (e.g., for body scans). For both scanning methods, technical specifications of the scanning sequences used should be optimized for the evaluation of the type and site of disease. The modality used at follow-up should be the same as was used at baseline, and the lesions should be measured/assessed on the same pulse sequence. Ideally, the same type of scanner should be used, and the image acquisition protocol should be followed as closely as possible to prior scans. Body scans should be performed with breath-hold scanning techniques, if possible.

Positron emission tomography (PET)-CT: Combined PET-CT is not always of optimal diagnostic CT quality for use with RECIST measurements. However, if the site can document that the CT performed as part of a PET-CT is of identical diagnostic quality to a diagnostic CT (with IV and oral contrast), then the CT portion of the PET-CT can be used for RECIST measurements and can be used interchangeably with conventional CT in accurately measuring cancer lesions over time.

Fluorodeoxyglucose (FDG)-PET: FDG-PET scanning is optional and may be used to complement CT scanning in assessment of progression (particularly possible 'new' disease). New lesions on the basis of FDG-PET imaging can be identified according to the following algorithm:

1. Negative FDG-PET at baseline, with a positive FDG-PET at follow-up is a sign of PD based on a new lesion.
2. No FDG-PET at baseline and a positive FDG-PET at follow-up: If the positive FDG-PET at follow-up corresponds to a new site of disease confirmed by CT, this is PD. If the positive FDG-PET at follow-up is not confirmed as a new site of disease on CT, additional follow-up CT scans are needed to determine if there is truly progression occurring at that site (if so, the date of PD will be the date of the initial abnormal FDG-PET scan). If the positive FDG-PET at follow-up corresponds to a pre-existing site of disease on CT that is not progressing on the basis of the anatomic images, this is not PD.
3. FDG-PET may be used to upgrade a response to a CR in a manner similar to a biopsy in cases where a residual radiographic abnormality is thought to represent fibrosis or scarring. The use of FDG-PET in this circumstance should be prospectively described in the protocol and supported by disease-specific medical literature for the indication. However, it must be acknowledged that both approaches may lead to false positive CR due to limitations of FDG-PET and biopsy resolution/sensitivity.

NOTE: A 'positive' FDG-PET scan lesion means one that is FDG avid with an uptake greater than twice that of the surrounding tissue on the attenuation corrected image.

Ultrasound is not useful in assessment of lesion size and should not be used as a method of measurement. If new lesions are identified by ultrasound in the course of the study, confirmation by CT or Mill is advised.

Cytology and histology techniques can be used to differentiate between PR and CR in rare cases (e.g., residual lesions in tumor types, such as germ cell tumors, where known residual benign tumors can remain).

The cytological confirmation of the neoplastic origin of any effusion that appears or worsens during treatment when the measurable tumor has met criteria for response or SD is mandatory to differentiate between response or SD (an effusion may be a side effect of the treatment) and PD.

Response Criteria

Evaluation of Target Lesions

CR: Disappearance of all target lesions. Any pathological lymph nodes (whether target or non-target) must have reduction in short axis to <10 mm.

PR: At least a 30% decrease in the sum of the diameters of target lesions, taking as reference the baseline sum diameters.

PD: At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (NOTE: the appearance of one or more new lesions is also considered progression).

SD: Neither sufficient shrinkage to qualify for PR nor sufficient increase to qualify for PD, taking as reference the smallest sum diameters while on study.

Evaluation of Non-Target Lesions

CR: Disappearance of all non-target lesions and normalization of tumor marker level. All lymph nodes must be non-pathological in size (<10 mm short axis).
NOTE: If tumor markers are initially above the upper normal limit, they must normalize for a patient to be considered in complete clinical response.

Non-CR/Non-PD: Persistence of one or more non-target lesion(s) and/or maintenance of tumor marker level above the normal limits.

PD: Appearance of one or more new lesions and/or unequivocal progression of existing non-target lesions. Unequivocal progression should not normally trump target lesion status. It must be representative of overall disease status change, not a single lesion increase.

Although a clear progression of "non-target" lesions only is exceptional, the opinion of the treating physician should prevail in such circumstances, and the progression status should be confirmed at a later time by the review panel (or PI).

Evaluation of Best Overall Response

The best overall response is the best response recorded from the start of the treatment until disease progression/recurrence (taking as reference for PD the smallest measurements recorded since the treatment started). The patient's best response assignment will depend on the achievement of both measurement and confirmation criteria. Best overall response is described in Table 2 for patients with measurable disease and in Table 3 for patients with non-measurable disease.

TABLE 2

Best Overall Response for Patients with Measurable Disease (i.e., Target Disease)

| Target Lesions | Non-Target Lesions | New Lesions | Overall Response | Best Overall Response when Confirmation is Required |
|---|---|---|---|---|
| CR | CR | No | CR | ≥4 weeks confirmation$^a$ |
| CR | Non-CR/Non-PD | No | PR | ≥4 weeks confirmation$^a$ |
| CR | Not evaluated | No | PR | |
| PR | Non-CR/Non-PD/ not evaluated | No | PR | |
| SD | Non-CR/Non-PD/ not evaluated | No | SD | Documented at least once ≥4 weeks from baseline no prior SD, PR, or CR |
| PD | Any | Yes or No | PD | |
| Any | PD$^b$ | Yes or No | PD | |
| Any | Any | Yes | PD | |

Abbreviations:
CR = complete remission;
SD = stable disease;
PD = progressive disease;
PR = partial response;
RECIST = Response Evaluation Criteria in Solid Tumors.

TABLE 2-continued

Best Overall Response for Patients with Measurable Disease (i.e., Target Disease)

| Target Lesions | Non-Target Lesions | New Lesions | Overall Response | Best Overall Response when Confirmation is Required |
|---|---|---|---|---|

$^a$Only for non-randomized studies with response as primary endpoint.
$^b$In exceptional circumstances, unequivocal progression in non-target lesions may be accepted as disease progression.
Note:
Patients with a global deterioration of health status requiring discontinuation of treatment without objective evidence of disease progression at that time should be reported as "symptomatic deterioration." Every effort should be made to document the objective progression even after discontinuation of treatment.
See RECIST v1.1 manuscript for further details on what is evidence of a new lesion.
NOTE:
For purposes of this trial, confirmation of response will occur at 6 weeks after the response-defining measurements rather than the 4-week point specified in the RECIST v1.1 criteria.

TABLE 3

Best Overall Response for Patients with Non-Measurable Disease (i.e., Non-Target Disease)

| Non-Target Lesions | New Lesions | Overall Response |
|---|---|---|
| CR | No | CR |
| Non-CR/non-PD | No | Non-CR/non-PD$^a$ |
| Not all evaluated | No | not evaluated |
| Unequivocal PD | Yes or No | PD |
| Any | Yes | PD |

Abbreviations:
CR = complete remission;
PD = progressive disease;
SD = stable disease
$^a$'Non-CR/non-PD' is preferred over 'stable disease' for non-target disease since SD is increasingly used as an endpoint for assessment of efficacy in some trials so to assign this category when no lesions can be measured is not advised Duration of Response Duration of overall response: The duration of overall response is measured from the time measurement criteria are met for CR or PR (whichever is first recorded) until the first date that recurrent or PD is objectively documented (taking as reference for PD the smallest measurements recorded since the treatment started).

The duration of overall CR is measured from the time measurement criteria are first met for CR until the first date that PD is objectively documented.

Duration of SD: The duration of SD is measured from the start of the treatment until the criteria for progression are met, taking as reference the smallest measurements recorded since the treatment started, including the baseline measurements.

Laboratory Assessments

Blood and urine samples for laboratory assessments will be collected at the time points specified in Table 4. Specific complete blood count (CBC) with differential, complete serum chemistry, and urinalysis assessments are listed in Table 10. Samples will be collected in accordance with the site's usual procedures and analyzed by the site's local laboratory for CBC with differential, complete serum chemistry, and urinalysis.

Laboratory tests for screening should be performed within 10 days prior to the first dose of treatment. After Cycle 1, predose laboratory procedures can be conducted up to 72 hours prior to dosing on Day 1 of each cycle. Results must be reviewed by the Investigator or qualified designee and found to be acceptable prior to each dose of study drug.

If a site is unable to collect all specimens due to low hemoglobin or other issues such as vein access, specimens should be collected in the following order if required at the visit:

Toxicity/safety specimens
Humoral (plasma- and serum-based) assays
Cellular (peripheral blood mononuclear cell [PBMC]-based) assays.

Laboratory Correlative Studies

Specimens will be collected for several planned correlative studies at specified time points. Many samples will be processed and stored, to be run in batches. When blood volume is limited, correlative studies will be considered secondary to tests needed to make clinical decisions. Also, testing may be delayed or omitted if collecting the specimens may pose a danger to the patient, if samples cannot be processed or assayed, or if results are determined to be non-essential to achieving the objectives of the study.

Correlative Studies with Biopsies

Collection of pretreatment tumor tissue (fresh biopsy via excisional, incisional, or core needle and large enough to show tissue architecture) is mandatory; if collecting pretreatment tissue is not possible (e.g., inaccessible or patient safety concern), submission of archived specimen is possible upon agreement from the Sponsor. Obtaining a post-treatment (second) biopsy is mandatory in order to achieve protocol objectives and to study the TME post-treatment but may be bypassed for patient safety reasons only after discussions with the Sponsor. Biopsy-based correlatives are considered exploratory. Prioritization of biopsy specimens will be made based on technical considerations that will be included in the Laboratory Manual, total number of samples acquired, and feasibility of correlative study based on the above considerations.

The pretreatment biopsy will be collected after all screening assessments have been performed and before the first dose of pembrolizumab and the fusion protein of SEQ ID NO: 1 on Cycle 1, Week 1, Day 1. The pretreatment specimen may be obtained up to 6 weeks (42 days) prior to initiation of treatment on Day 1, provided study informed consent has been obtained or the biopsy was performed as part of routine patient care. The post-treatment (second) biopsy will be performed on the same or similar tumor site during the first cycle of therapy at C1D12 or at any time from C1D8 through C1D19. Fine needle aspirates are not allowed for tissue sampling but may be used to localize active disease prior to tissue sampling. The biopsies will be collected according to clinical site standard operating procedures (SOPs).

Tumor PD-L1 Expression and Multiparameter Immunohistochemistry

Because tumor-infiltrating immune cells are associated with clinical outcomes, infiltrates from pre-treatment tumor tissue and from biopsies taken during treatment will be assessed by IHC to determine the extent and nature of T-cell infiltration and of the immune milieu of TME. PD-L1 expression will be quantitated in the baseline formalin-fixed paraffin-embedded tumor specimens. Additionally, to further characterize the immune cell infiltrate, tumors may also be assayed by IHC for a variety of other markers, including but not limited to CD56 and CD16 (NK cells), CD68, CD8, PD-1, TIM-3, and LAG3.

Whole Genome, Whole Exome, and RNA Sequencing

Genomic sequencing of tumor cells from tissue relative to non-tumor cells from whole blood will be profiled to identify the genomic variances that may contribute to response or disease progression and provide an understanding of molecular abnormalities. If applicable, mutation burden will be quantified and analyzed by subgroups of patients with HPV sequences or exposure to environmental factors such as history of tobacco use. Gene expression will be analyzed by RNA sequencing and compared to deoxyribonucleic acid (DNA) mutations. Protein expression levels may be analyzed for protein-coding genes of interest based on mutation status or expression results.

All genomic and transcriptomic analyses will be retrospective and exploratory. To determine the genomic profile of patients' tumors and to identify gene mutations, gene amplifications, RNA-expression levels, and protein-expression levels, correlations between genomic/transcriptomic profiles and efficacy outcomes will be assessed. Tumor mutational burden may be assessed by FOUNDATION-ONE® or other TMB analysis, as appropriate.

Gene Expression Profiling of Biopsy

Ribonucleic acid expression analyses will be performed using nanoString or similar technology to identify potential signatures correlating with tumor T-cell infiltration patterns and clinical response. While the nanoString technology does not distinguish the source of nucleic acid (tumor cells vs lymphocytes vs other infiltrating cells), distinct patterns from the unseparated cell mixture may correlate with clinical outcomes. These gene expression profiles may provide an additional detailed phenotype to guide correlative investigation.

T-Cell Clonality

Assessment of T-cell clonality will involve TCR sequencing of tumor-infiltrating lymphocytes (TIL) where pretreatment and post-treatment biopsies are available. T-cell receptor beta chain (TCRB) high throughput sequencing will be done on genomic DNA extracted and polymerase chain reaction (PCR) amplified from fixed tumor samples (pre- and post-treatment) using the immunoSEQ™ human TCRB (hsTCRB) kit (Adaptive Biotechnologies) and sequenced on the Illumina MiSeq platform either using shared resource facilities (Fred Hutchinson Cancer Research Center [FHCRC]) or contracted out to Adaptive Biotechnologies (Seattle) or other similar contractor.

Correlative Studies with Blood Draws

Immunophenotyping of Peripheral Blood Mononuclear Cells

Blood samples will be collected at various points during the study. The change in frequency of T cells (CD3+ CD4+ CD56– and CD3+ CD8+ CD56–) and NK cells (CD3– CD56+) resulting from the fusion protein of SEQ ID NO: 1 treatment in the presence of pembrolizumab will be evaluated by flow cytometry using whole blood and/or PBMC. Samples will be sent to the Central Immune Monitoring Laboratory (CIML) for analysis. These data will not be used for making clinical decisions on this protocol. For this, the CIML will immunophenotype cells in whole blood using a 22-color whole-blood phenotyping panel. This panel characterizes and quantifies the absolute number and proportion of memory and naïve T-cell subsets using antibodies to CD4, CD8, CD45RA, CCR7, CD28, CD127, and CD62L; of Tregs using antibodies to CD127 and CD25; and the activation state of T cells using antibodies to CTLA-4, PD-1, HLA-DR, Tim-3, Lag-3, and TIGIT. The same panel will assess and quantify absolute numbers of NK cells (CD56+ CD3−), NK T cells (CD56+ CD3+), B cells (CD19+), monocytes (CD16+), dendritic cells (HLA-DR+CD123+ or CD11c+), and neutrophils (CD14+).

Peripheral blood myeloid-derived suppressor cells may also be assessed in a separate panel using HLA-DR, CD11b, and CD33 along with other lineage markers.

For the phenotypic analyses, the absolute number and percentage of cells positive for the marker and/or mean fluorescence intensity (MFI) at time points after study drug administration will be compared to baseline and the change will be calculated as #after/#baseline, % after/% baseline or MFI after/MFI baseline.

T- and NK-Cell Function Assays

To assess T- and NK-cell proliferative function, intracellular Ki-67 expression will be analyzed in the context of phenotypic characterization of CD4+ and CD8+ $\alpha/\beta$ and $\gamma/\delta$ T cells and CD3− CD56+ NK cells among PBMC.

The fusion protein of SEQ ID NO: 1 effects on NK-cell function will be measured using flow cytometric expression of the degranulation marker CD107a and by cytokine (i.e., IFN-$\gamma$ and tumor necrosis factor-$\alpha$) secretion. The ability of NK cells to respond to defined stimuli (plate-bound anti-CD16, IL12 plus IL18, and a standard NK-stimulatory cell line, K562) leading to degranulation of NK cells or secretion of cytokines will be compared before and after SEQ ID NO: 1 treatment. Data will be evaluated for changes in degranulation and cytokine secretion over time under both unstimulated and stimulated (plate-bound anti-CD16, IL-12 plus IL-18, and a standard NK-stimulatory cell line, K562) conditions. After accounting for background degranulation and cytokine secretion, the percentage of CD3− CD56+ NK cells expressing CD107a or cytokines at time points after dosing will be divided by the results at the pretreatment time point to determine the fold difference between the two. Other conditions and markers may be tested to obtain optimal evaluations of NK-cell and T-cell function. These assays will be performed at the CIML or University of Washington, Seattle, or other agreed upon vendor.

Plasma Cytokine Assays

Changes in the plasma cytokine concentration of pro-inflammatory and immunosuppressive cytokines may correlate with the administration of the fusion protein of SEQ ID NO: 1. This will also serve as an important assessment to verify and compare the treatment effect of the fusion protein of SEQ ID NO: 1 with pembrolizumab relative to previous studies. Samples from baseline and post-treatment will be collected 4 to 6 hours post-fusion protein of SEQ ID NO: 1 administration and tested in multiplex cytokine enzyme-linked immunosorbent assays (ELISA or Luminex). Plasma for cytokines and serum for anti-drug antibodies (ADAs)/immunogenicity will both be processed locally, batch-shipped to the CIML, and distributed to assay site(s).

Kynurenine/Tryptophan Ratios and Plasma Arginine Levels

Kynurenine to tryptophan ratios in plasma will be measured at baseline, during treatment, and at end of treatment in this protocol to analyze, in patients who have failed clinical response to treatment, whether failure may be associated with increased Kyn/Trp levels.

Plasma arginine levels will be measured at baseline, during treatment, and at end of treatment in this protocol to analyze, in patients who have failed clinical response to treatment, whether failure may be associated with increased arginine levels in plasma.

Immunogenicity of the Fusion Protein of SEQ ID NO: 1

Patients will be monitored for the presence and development of auto-antibodies to the fusion protein of SEQ ID NO: 1. Serial serum samples will be assessed from baseline, at Day 1 of each cycle, and 14 days after the last treatment.

All patients who met eligibility criteria, had analyzable specimens, and received at least 1 dose of the fusion protein of SEQ ID NO: 1 will be included in the immunogenicity analyses. Subset analysis will prospectively be analyzed for all patients completing each complete cycle of the fusion protein of SEQ ID NO: 1.

Immune testing will follow a similar scheme with each cycle of the fusion protein of SEQ ID NO: 1. Serum samples for evaluation of anti-SEQ ID NO: 1 antibody induction will be obtained from each patient at predetermined time points. A validated electrochemiluminescence method using the Meso Scale Discovery platform will be used for the detection of ADAs to the fusion protein of SEQ ID NO: 1 in human serum. The assessment of immune response induction for each study patient will be based on the comparison of the predose and postdose sample results. Remaining serum samples will be stored for potential analysis of anti-pembrolizumab antibody induction at a future date.

NOTE: Blood collection for all immunogenicity samples required must be drawn before the patient receives the fusion protein of SEQ ID NO: 1 on any scheduled day.

Microbiome Analysis

Fecal samples will be collected from patients at baseline and will be used for taxonomic profiling via 16S rRNA gene sequencing and metagenomics WGS sequencing. Fecal samples will be collected and stored using standard, at-home stool collection procedures, and the landscape of the gut microbiome will be assessed. Sequencing data will be analyzed and compared to clinical responses to determine whether response or non-response to treatment can be correlated with specific microbiota. Assays will be performed in collaboration with Dr. David Fredricks (FHCRC) or other agreed upon vendor.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Example 2—Clinical Outcomes of Ovarian Cancer Patients Treated with the Fusion Protein of SEQ ID NO: 1 in Combination with an Anti-PD-1 Antibody: ARTISTRY-1 Trial Methods: ARTISTRY-1 is an ongoing multicohort phase 1/2 trial exploring treatment with the fusion protein of SEQ ID NO: 1 delivered intravenously (IV) as monotherapy and in combination with the anti-PD-1 antibody, pembrolizumab. Ovarian cancer (OC) patients were enrolled into a cohort of patients with mixed anti-PD-1/PD-L1 unapproved tumor types who had progressed on prior chemotherapy. OC patients received IV of the fusion protein of SEQ ID NO: 1 (3 µg/kg) on days 1-5 and pembrolizumab (200 mg) on day 1 of a 21-day cycle. Outcomes presented include antitumor activity (RECIST v1.1) and safety. To understand the tumor microenvironment, pretreatment and on-treatment biopsies were collected.

Results: Fourteen predominantly platinum-resistant and heavily pretreated patients with OC were enrolled. Patients received a median of 5 (range, 2-11) prior therapeutic regimens; all were previously treated with platinum-based therapy. Among 13 patients with ≥1 assessment, 9 experienced disease control and 4 experienced disease progression. Three BRCA wild-type and anti-PD-1/PD-L1-naïve patients experienced an objective response, including 1 complete response, 1 partial response (PR), and 1 unconfirmed PR. Five patients experienced tumor burden reductions (Table 5). Treatment-related adverse events at the doses tested were generally transient and manageable. Overall, the combination with the fusion protein of SEQ ID NO: 1 did not demonstrate any additive toxicity to that already established with pembrolizumab alone. Additional safety and efficacy data are being collected in ongoing cohorts. Fusion protein of SEQ ID NO: 1 monotherapy also increased markers of lymphocyte infiltration in 1 paired biopsy (1 of 1; on-treatment biopsy at cycle 2); CD8$^+$ T cell density and PD-L1 tumor proportion score increased 5.2- and 11-fold, respectively, demonstrating the immunostimulatory impact of the fusion protein of SEQ ID NO: 1 on the tumor microenvironment and supporting the rationale of further evaluating the fusion protein of SEQ ID NO: 1 with pembrolizumab (FIGS. 4A-4C).

TABLE 5

Summary of response observations among patients with ovarian cancer

| Patient | Age (years) | Prior Therapies | Max. Reduction of Target Lesions (%) | OR[a] | CA125 (U/mL) Response From Baseline | Time on Fusion protein of SEQ ID NO: 1 (Weeks) |
|---|---|---|---|---|---|---|
| 1 | 48 | CBP/PAC/BEV, CDDP/GEM, CBP/PLD, PCA, CBP/DOC | 70.0 | CR[b] | Normalized from 282 to 24.5 at cycle 4 | 81+[c] |
| 2 | 83 | CBP/PAC/DOC, CBP/DOC/NIR/TAM | 76.3 | PR | Normalized from 125 to 16 at cycle 4 | 23+[c] |
| 3 | 60 | CBP/PAC, CBP/PLD, CBP/BEV, PAC/BEV, BEV, PLD | 44.7 | uPR | Reduced, from 1400 to 260 at cycle 4 | 34 |
| 4 | 75 | CBP/PAC, PLD/BEV, CBP/GEM, TOP, NIR | 21.9 | SD | Reduced from 493 to 245 at cycle 5 | 14+[c] |
| 5 | 83 | CBP/PAC, CBP, CBP/PAC/CAP, CBP/PLD, CBP/PLD | 18.3 | SD | Normal at baseline at 10.6 | 21+[c] |

[a]As assessed by the investigator.
[b]CR due to node shrinkage to <10 mm short axis, which is considered normal.
[c]Patient is currently ongoing in the trial.
BEV, bevacizumab;
CAP, capecitabine;
CBP, carboplatin;
CDDP, cisplatin;
CR, confirmed response;
DOC, docetaxel;
GEM, gemcitabine;
max, maximum;
NIR, niraparib;
OR, objective response;
PAC, paclitaxel;
PCA, paclitaxel albumin;
PD, progressive disease;
PLD, pegylated liposomal doxorubicin hydrochloride;
SD, stable disease;
TAM, tamoxifen,
TOP, topotecan;
uPR, unconfirmed partial response.

Conclusions: Combination treatment of the fusion protein of SEQ ID NO: 1 and an anti-PD-1 antibody demonstrated an acceptable safety profile and provided clinical activity by durable tumor shrinkage and disease stabilization in patients with recurrent OC.

Example 3—Subcutaneously Administered Fusion Protein of SEQ ID NO: 1 as Monotherapy and in Combination with Pembrolizumab in Patients with Advanced Solid Tumors: ARTISTRY-2

Methods: ARTISTRY-2 (NCT03861793) is an ongoing phase 1/2 study of subcutaneous (SC) delivery of the fusion protein of SEQ ID NO: 1 with and without the anti-PD1 antibody, pembrolizumab. In phase 1, cohort-specific doses of SC fusion protein of SEQ ID NO: 1 were administered on either an every-7-day [q7d] or every-21-day [q21d] schedule during a 6-week lead-in period, followed by combination with IV pembrolizumab 200 mg q21d. Each patient assigned to a given cohort received the fusion protein of SEQ ID NO: 1 at a single dose level and on a schedule of either q7d or q21d. Safety, tolerability, dose-limiting toxicities (DLTs), and pharmacokinetics/pharmacodynamics from dose escalation.

Results: 38 patients have been treated with the fusion protein of SEQ ID NO: 1 across 7 assigned cohorts, with SC doses ranging from 0.3 mg to 10 mg (median age, 61.5 [28-82] years; median number of prior therapies 4 [0-17]; 45% were previously treated with immunotherapy). 25 patients completed monotherapy and initiated combination therapy. Median duration of treatment was 64.5 (1-506) days. Systemic exposure to the fusion protein of SEQ ID NO: 1 increased with increasing dose, resulting in a dose-dependent increase in circulating natural killer and $CD8^+$ T cells, without significant impact on regulatory T cells. Overall, treatment-emergent adverse events (TEAEs) occurred in 33 (86.8%) patients. Treatment-related AEs (TRAEs; investigator assessed) occurred in 32 (84.2%) patients, and the most common TRAEs are presented in Table 6. One patient experienced a serious TRAE, a grade 3 tumor flare manifesting as colonic obstruction; a maximum tolerated dose has not been reached.

TABLE 6

Most common (≥20%) TRAEs overall and by dose schedule

| | q7d | | | | q21d | | | q7d + q21d |
|---|---|---|---|---|---|---|---|---|
| | 0.3 mg (n = 7) | 0.6 mg (n = 3) | 1 mg (n = 7) | 3 mg (n = 7) | 1 mg (n = 4) | 3 mg (n = 4) | 10 mg (n = 6) | Overall (N = 38) |
| Patients with ≥1 fusion protein of SEQ ID NO: 1-related TRAEs, n (%) | 7 (100) | 2 (66.7) | 7 (100) | 5 (71.4) | 4 (100) | 4 (100) | 3 (50) | 32 (84.2) |
| Injection site reactions[a], n (%) | 6 (85.7) | 1 (33.3) | 3 (42.9) | 4 (57.1) | 4 (100) | 3 (75) | 2 (33.3) | 23 (60.5) |
| Pyrexia, n(%) | 4 (57.1) | 0 | 2 (28.6) | 4 (57.1) | 0 | 3 (75) | 2 (33.3) | 15 (39.5) |
| Lymphopenia, n (%) | 1 (14.3) | 0 | 4 (57.1) | 3 (42.90) | 2 (50.0) | 1 (25.0) | 2 (33.3) | 13 (34.2) |
| Chills, n (%) | 3 (42.9) | 0 | 1 (14.3) | 3 (42.9) | 0 | 3 (75.0) | 2 (33.3) | 12 (31.6) |
| Fatigue, n (%) | 4 (57.1) | 0 | 1 (14.3) | 2 (28.6) | 1 (25.0) | 1 (25.0) | 1 (16.7) | 10 (26.3) |
| Nausea, n (%) | 4 (57.1) | 0 | 0 | 1 (14.3) | 0 | 2 (50) | 2 (33.3) | 9 (23.7) |

[a]Injection site reactions include erythema, reaction, pruritus, pain, swelling, irritation, inflammation, and warmth at the injection site.

Conclusions: The SC safety profile is consistent with known and anticipated pharmacologic effects of the fusion protein of SEQ ID NO: 1. Consistent with IV dosing, the SC administration of the fusion protein of SEQ ID NO: 1 q7d or q21d maintained the desired immune responses as demonstrated by pharmacodynamic outcomes. Potentially lower rates of fever and chills observed, relative to IV dosing, are presumed to be consistent with lower peak concentrations achieved via the SC route.

Example 4—Circularly Permuted (cp) IL-2:IL-2Rα Fusion Protein in Combination with Immune Checkpoint Inhibitors in Tumor-Bearing Mice MC38 Tumor-Bearing Mice The study design shown below in Table 7 was implemented for MC38 colorectal tumor model.

TABLE 7

Study design implemented for MC38 colorectal tumor model

| Group | N | Agent | Formulation dose | Route | Schedule |
|---|---|---|---|---|---|
| 1 | 10 | vehicle 1 // vehicle 2 | na // na | sc // ip | days 6, 10, 14, 18, 22 // biwkx2 (days 1, 4, 8, 11) |
| 2 | 10 | Fusion protein of SEQ ID NO: 2 // vehicle 2 | 9 mg/kg // na | sc // ip | days 6, 10, 14, 18, 22 // biwkx2 (days 1, 4, 8, 11) |
| 3 | 10 | vehicle 1 // anti PD-1 (RMP1-14) | na // 100 μg | sc // ip | days 6, 10, 14, 18, 22 // biwkx2 (days 1, 4, 8, 11) |
| 4 | 10 | Fusion protein of SEQ ID NO: 2 // anti PD-1 (RMP1-14) | 9 mg/kg // 100 μg | sc // ip | days 6, 10, 14, 18, 22 // biwkx2 (days 1, 4, 8, 11) |
| 5 | 10 | vehicle 1 // anti CTLA-4 (9D9) // anti CTLA-4 (9D9) | na // 100 μg // 50 μg | sc // ip // ip | days 6, 10, 14, 18, 22 // day 1 // day 4, 7 |
| 6 | 10 | Fusion protein of SEQ ID NO: 2 // anti CTLA-4 (9D9) // anti CTLA-4 (9D9) | 9 mg/kg // 100 μg // 50 μg | sc // ip // ip | days 6, 10, 14, 18, 22 // day 1 // day 4, 7 |

Figure 5A:
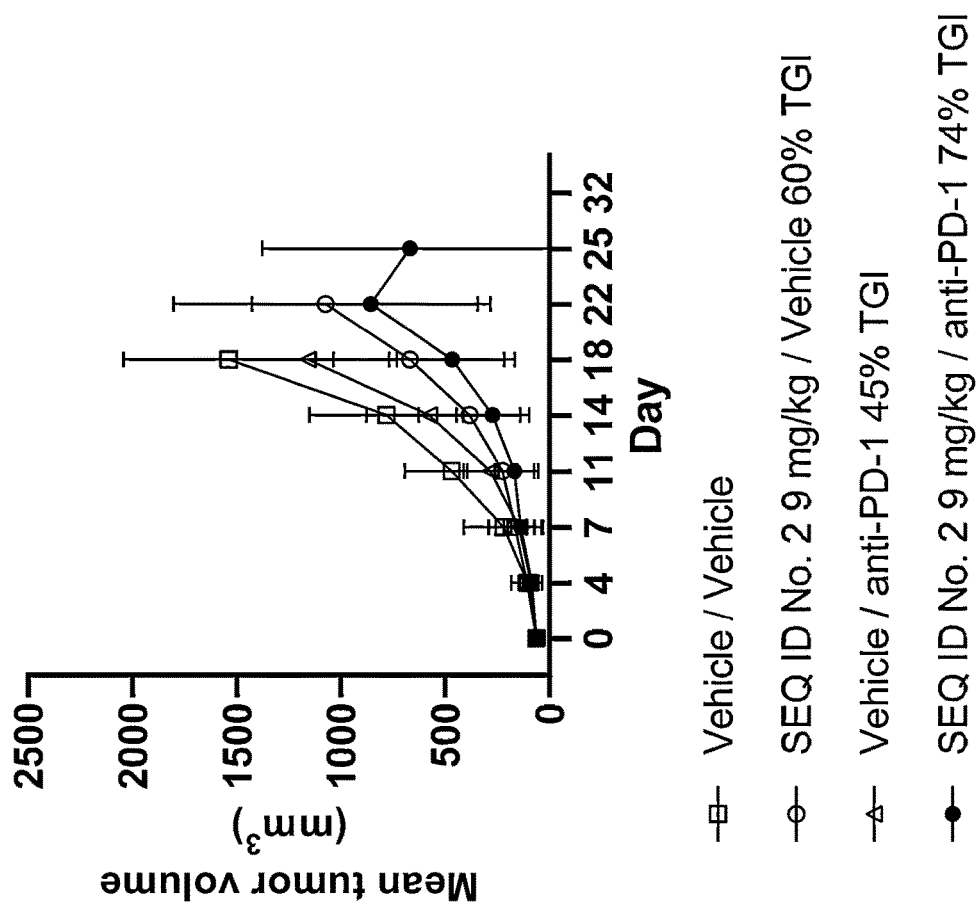
FIGS. 5A and 5B graphically depict mean tumor volume (FIG. 5A) and survival (FIG. 5B) in MC38 colorectal tumor model mice receiving: the fusion protein of SEQ ID NO: 2 in combination with an anti-PD-1 antibody; the fusion protein of SEQ ID NO: 2 alone; the anti-PD-1 antibody alone; or a vehicle control.
Figure 5B:
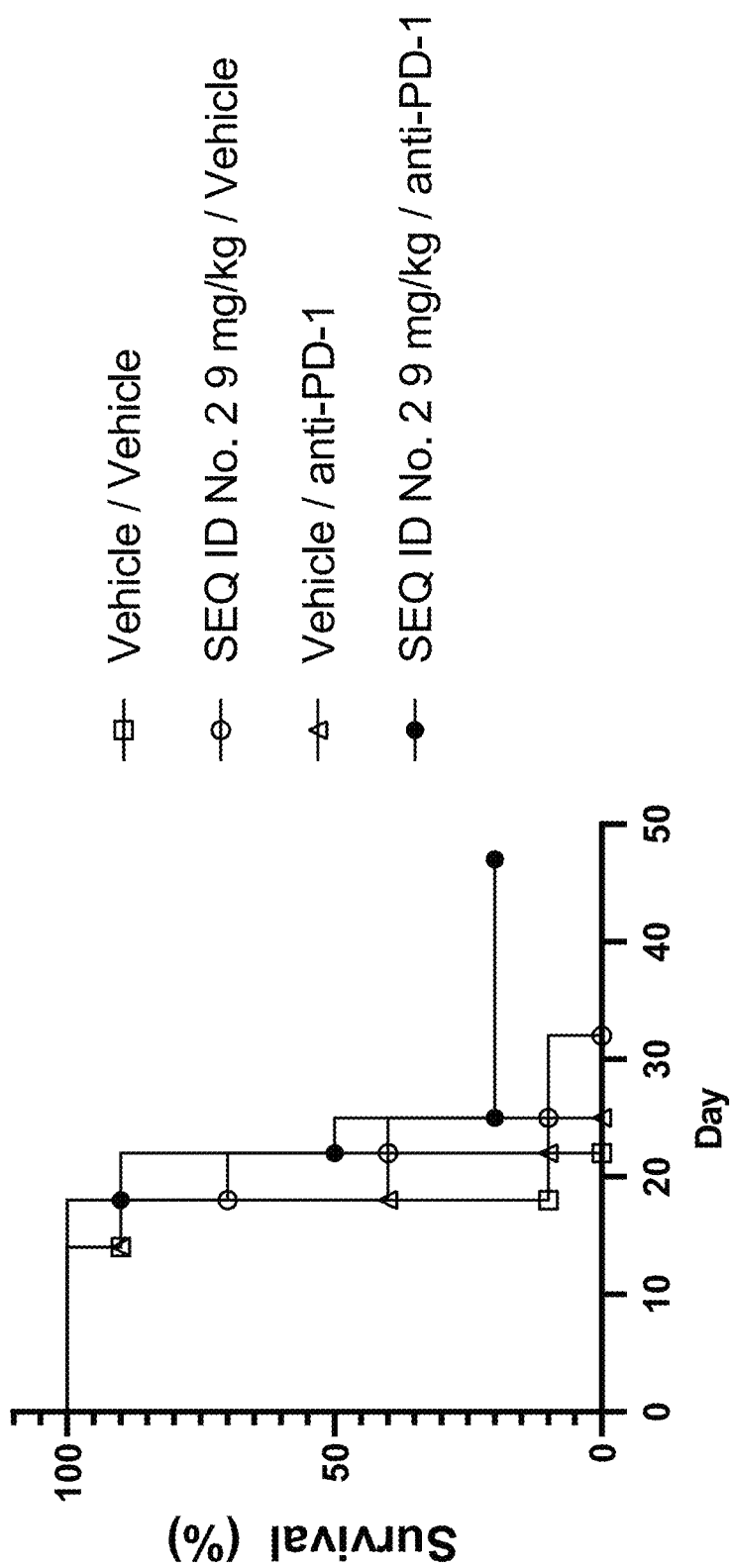
Figure 6A:
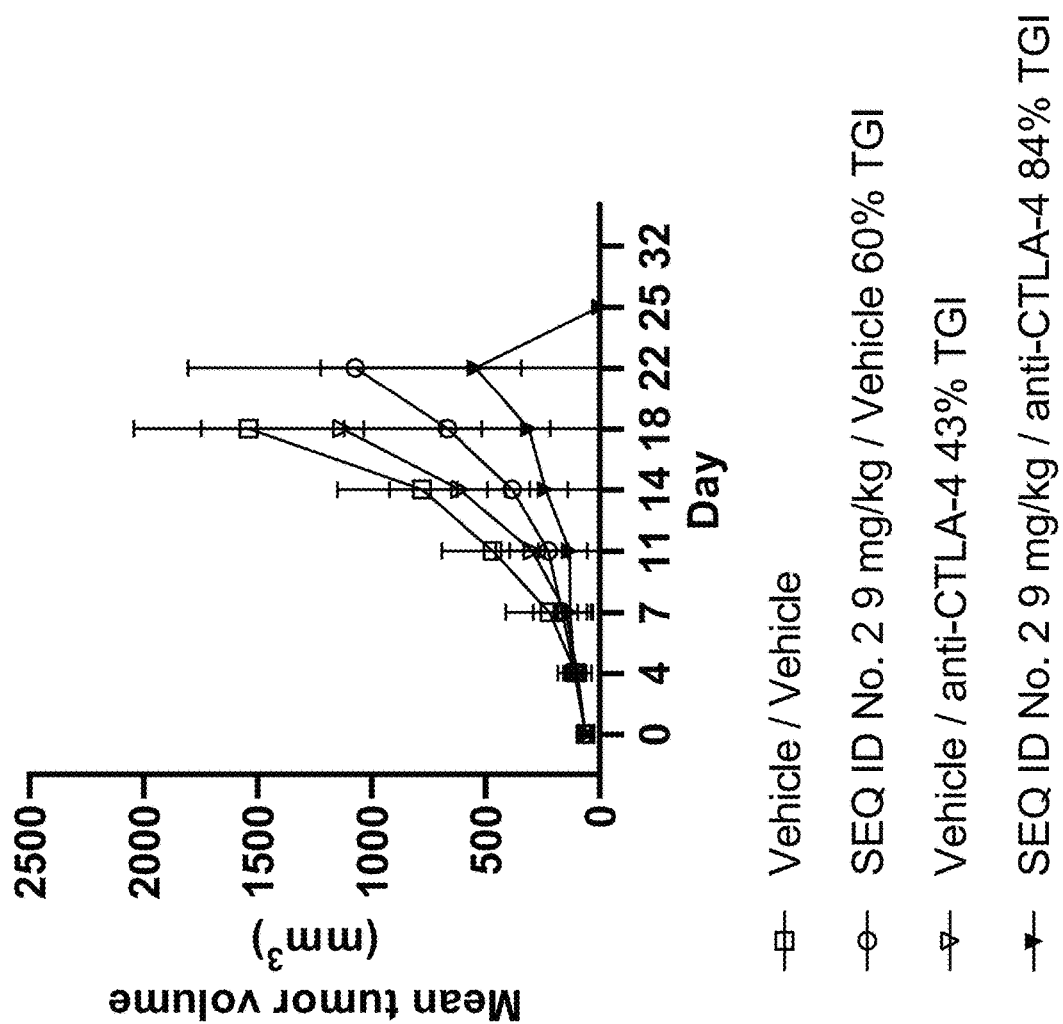
FIGS. 6A and 6B graphically depict mean tumor volume (FIG. 6A) and survival (FIG. 6B) in MC38 colorectal tumor model mice receiving: the fusion protein of SEQ ID NO: 2 in combination with an anti-CTLA-4 antibody; the fusion protein of SEQ ID NO: 2 alone; the anti-CTLA-4 antibody alone; or a vehicle control.
Figure 6B:
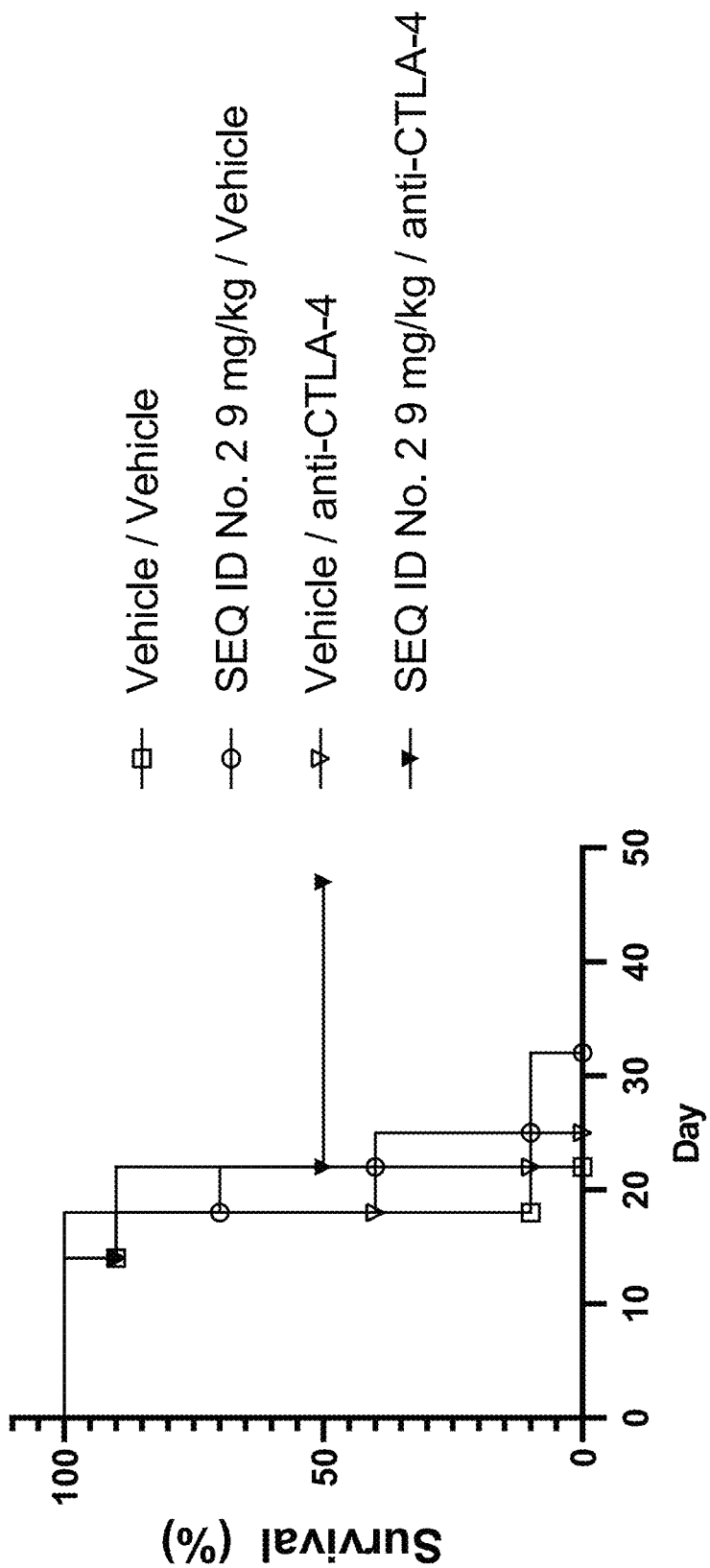

N = number of mice in study;
na = not applicable;
sc = subcutaneous;
ip = intraperitoneal The fusion protein of SEQ ID NO: 2 is the murine ortholog of the fusion protein of SEQ ID NO: 1. When SEQ ID NO: 2 was combined with the anti-PD-1 antibody, tumor growth inhibition (TGI) was increased from 45-60% for monotherapy treatments to 74% for combination therapy. Combination treatment also resulted in 2 complete responses (FIG. 5A and FIG. 5B). When the fusion protein of SEQ ID NO: 2 was combined with the anti-CTLA-4 antibody, TGI was increased from 43-60% for monotherapy treatments to 84% for combination therapy. Combination treatment also resulted in 5 complete responses (FIG. 6A and FIG. 6B).

Overall, the results demonstrate that the combination of the cpIL-2:IL-2Rα fusion protein and an immune checkpoint inhibitor (e.g., anti-PD-1 or anti-CTLA-4) enhance anti-tumor responses, such as in colorectal cancer.

B16F10 Tumor-Bearing Mice

The study design shown below in Table 8 was implemented for MC38 melanoma tumor model.

TABLE 8

Study design implemented for B16F10 melanoma tumor model

| Group | N | Agent | Active dose | Route | Schedule |
|---|---|---|---|---|---|
| 1 | 12 | vehicle 1 // vehicle 1 | na // na | sc // ip | 5/2/5/2/5 (start on day 6) // biwk x 3 |
| 2 | 12 | Fusion protein of SEQ ID NO: 2 // vehicle 1 | 9 mg/kg // na | sc // ip | days 6, 10, 14, 18, 22, 26 // biwk x 3 |
| 3 | 12 | vehicle 1 // anti-CTLA-4 9D9-AKM // anti-CTLA-4 9D9-AKM | na // 100 μg/animal // 50 μg/animal | sc // ip // ip | 5/2/5/2/5 (start on day 6) // day 1 // days 4, 7 |
| 4 | 12 | Fusion protein of SEQ ID NO: 2 // anti-CTLA-4 9D9-AKM // anti-CTLA-4 9D9-AKM | 9 mg/kg // 100 μg/animal // 50 μg/animal | sc // ip // ip | days 6, 10, 14, 18, 22, 26 // day 1 // days 4, 7 |

Figure 7A:
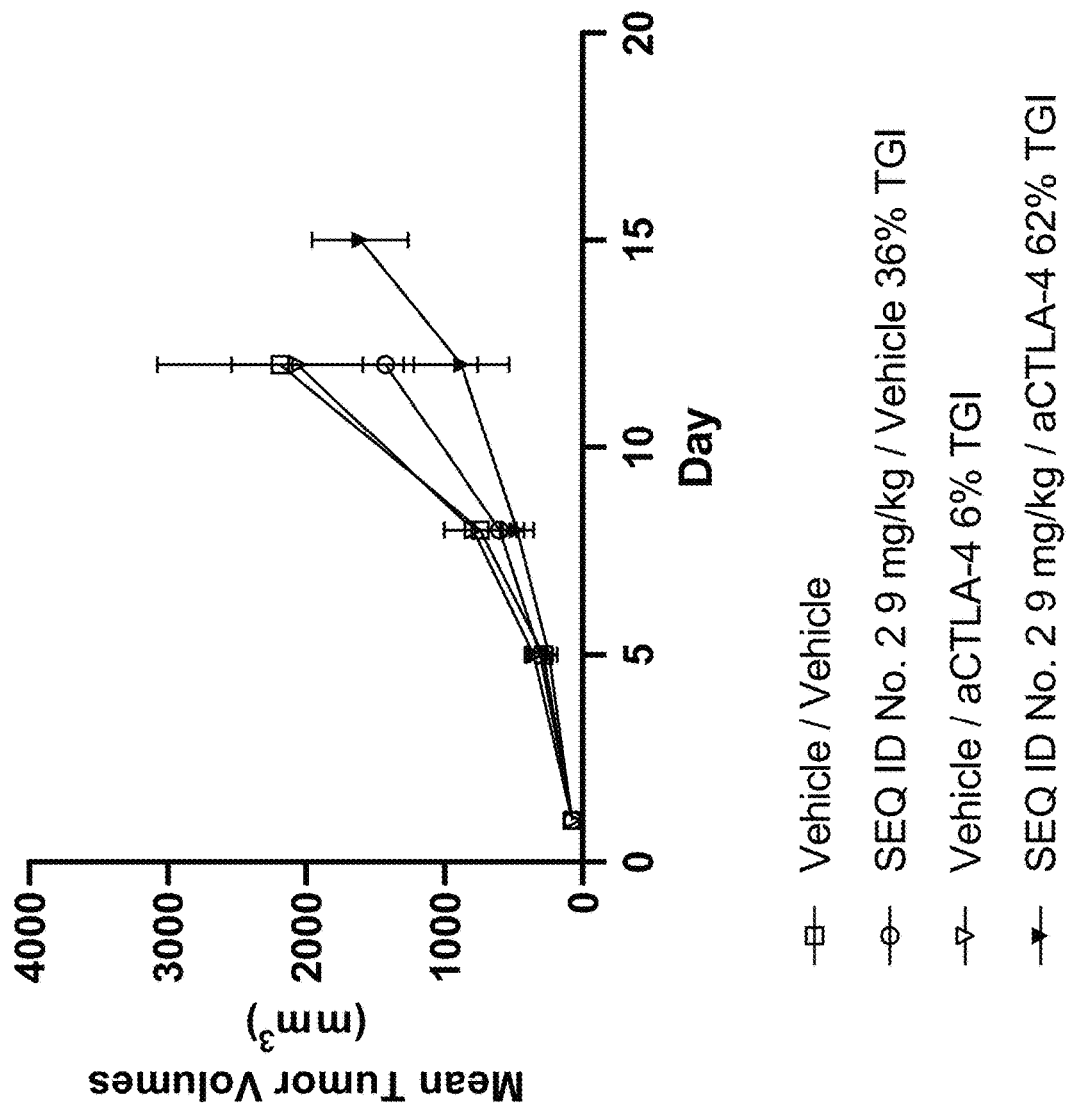
FIGS. 7A and 7B graphically depict mean tumor volume (FIG. 7A) and survival (FIG. 7B) in B16F10 melanoma tumor model mice receiving: the fusion protein of SEQ ID NO: 2 in combination with an anti-CTLA-4 antibody; the fusion protein of SEQ ID NO: 2 alone; the anti-CTLA-4 antibody alone; or a vehicle control.
Figure 7B:
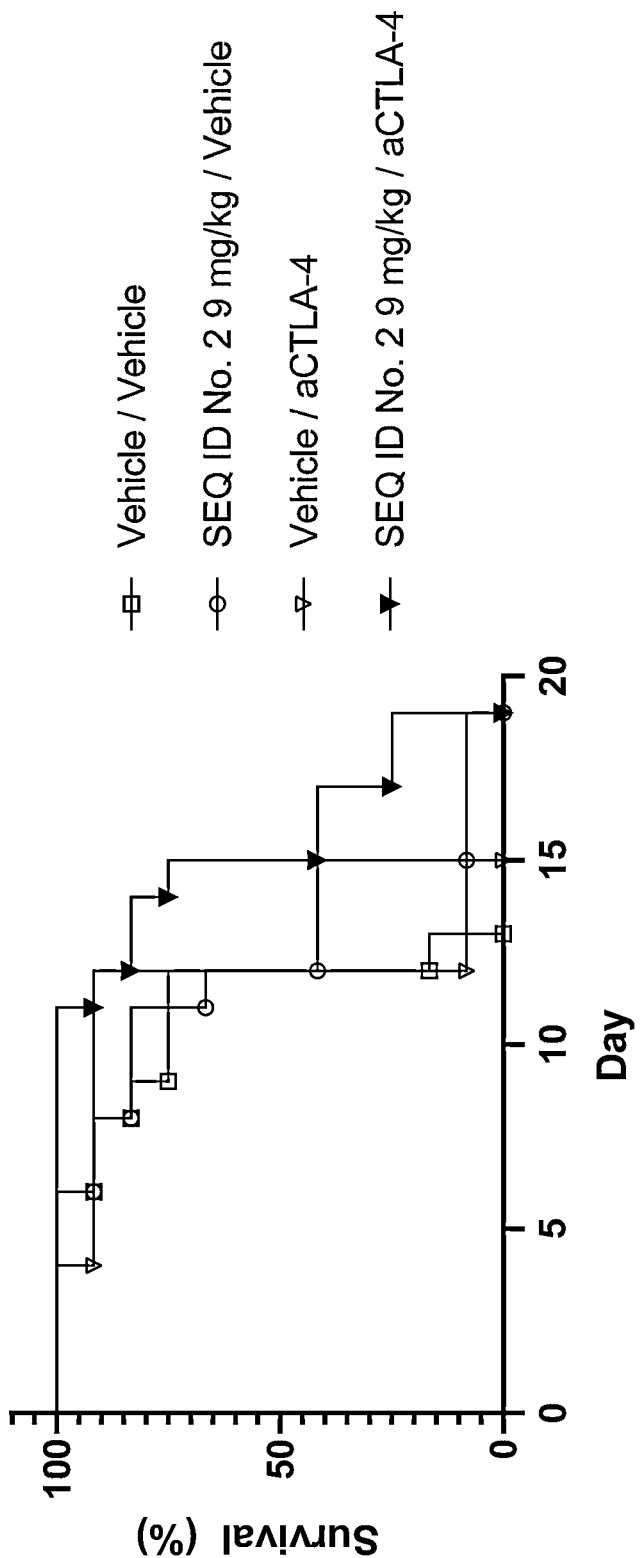

When the fusion protein of SEQ ID NO: 2 was combined with the anti-CTLA-4 antibody, TGI was increased from 3-36% for monotherapy treatments to 62% for combination therapy (FIG. 7A and FIG. 7B).

EMT-6 Tumor-Bearing Mice

The study design shown below in Table 9 was implemented for EMT-6 breast tumor model.

TABLE 9

Study design implemented for EMT-6 breast tumor model

| Group | N | Agent | Active dose | Route | Schedule |
|---|---|---|---|---|---|
| 1 | 10 | vehicle 1 // vehicle 1 | na // na | sc // ip | 5/2/5 (start on day 5) // biwk x 2 (start on day 5) |
| 2 | 10 | Fusion protein of SEQ ID NO: 2 // vehicle 1 | 0.8 mg/kg // na | sc // ip | 5/2/5 (start on day 10) // biwk x 2 (start on day 5) |
| 3 | 10 | vehicle 1 // anti-PD-1 RMP1-14-AKM | na // 100 μg/animal | sc // ip | 5/2/5 (start on day 10) // biwk x 2 (start on day 5) |
| 4 | 10 | Fusion protein of SEQ ID NO: 2 // anti-PD-1 RMP1-14-AKM | 0.8 mg/kg // 100 μg/animal | sc // ip | 5/2/5 (start on day 10) // biwk x 2 (start on day 5) |
| 5 | 10 | vehicle 1 // vehicle 1 | na // na | sc // ip | days 6, 10, 14, 18, 22, 26 // biwk x 3 |
| 6 | 10 | Fusion protein of SEQ ID NO: 2 // vehicle 1 | 9 mg/kg // na | sc // ip | days 6, 10, 14, 18, 22, 26 // biwk x 3 |
| 7 | 10 | vehicle 1 // anti-CTLA-4 9D9-AKM // anti-CTLA-4 9D9-AKM | na // 100 μg/animal // 50 μg/animal | sc // ip // ip | days 6, 10, 14, 18, 22, 26 // day 1 // days 4, 7 |
| 8 | 10 | Fusion protein of SEQ NO: 2 // anti-CTLA-4 9D9-AKM // anti-CTLA-4 9D9-AKM | 9 mg/kg // 100 μg/animal // 50 μg/animal | sc // ip // ip | days 6, 10, 14, 18, 22, 26 // day 1 // days 4, 7 |

Figure 8A:
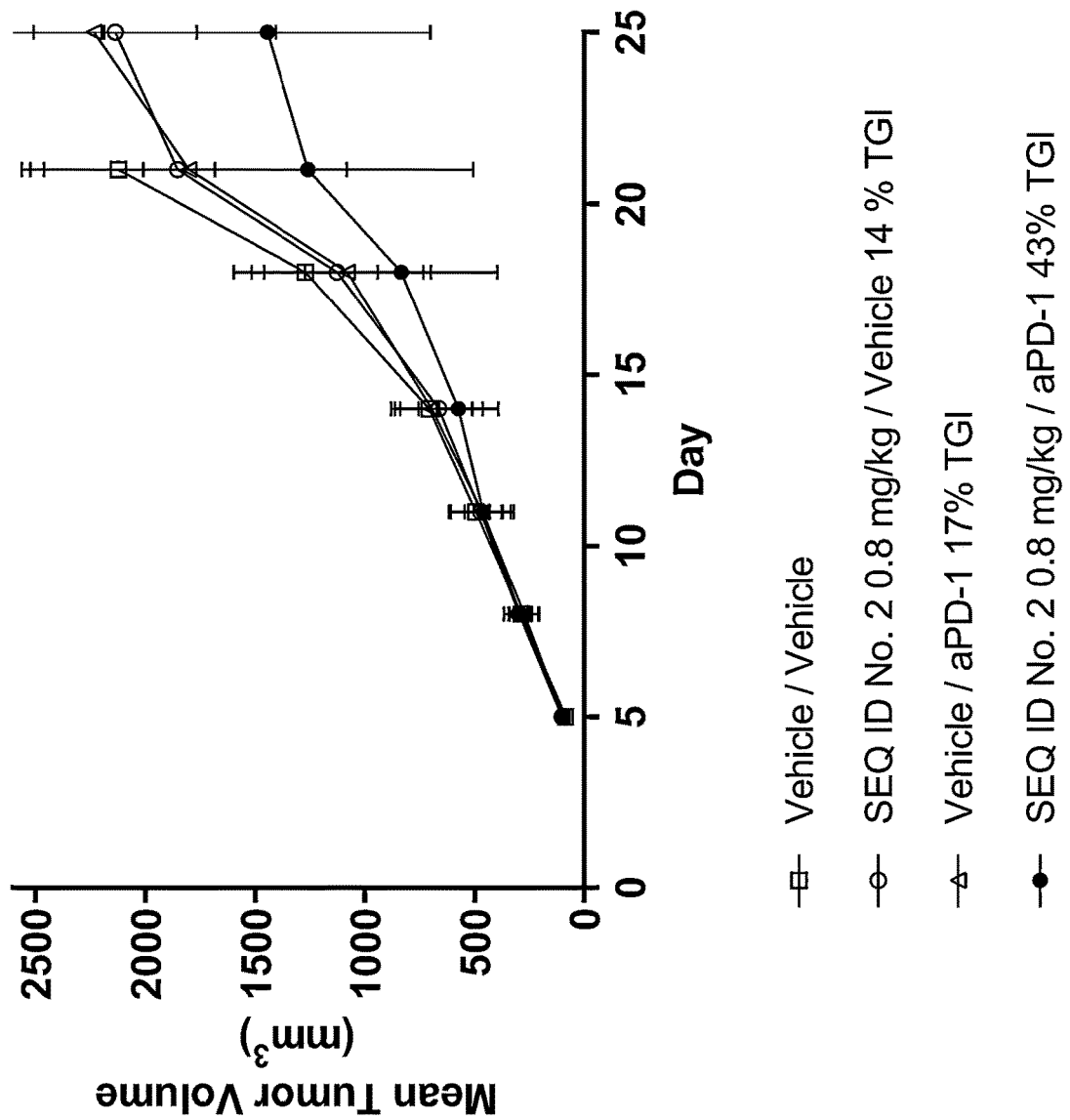
FIGS. 8A and 8B graphically depict mean tumor volume (FIG. 8A) and survival (FIG. 8B) in EMT-6 breast tumor model mice receiving: the fusion protein of SEQ ID NO: 2 in combination with an anti-PD-1 antibody; the fusion protein of SEQ ID NO: 2 alone; the anti-PD-1 antibody alone; or a vehicle control.
Figure 8B:
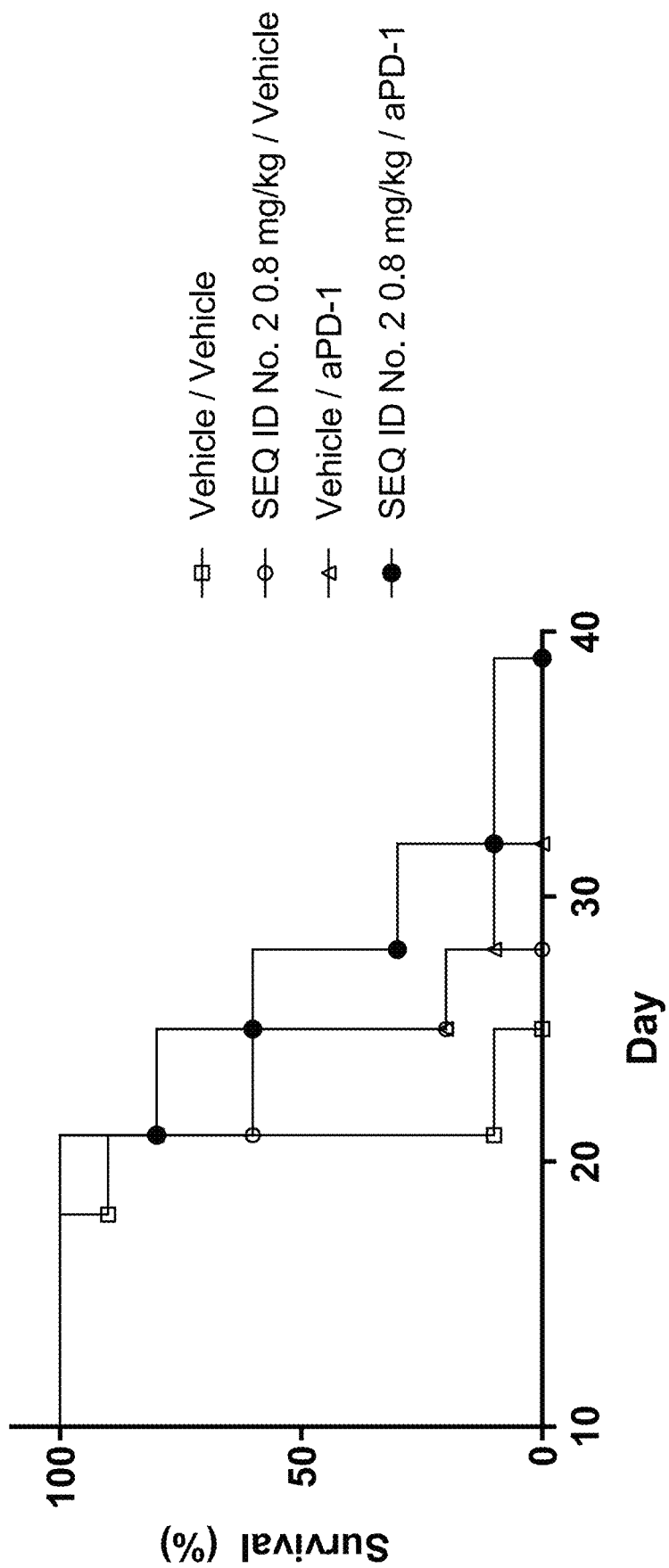
Figure 9B:
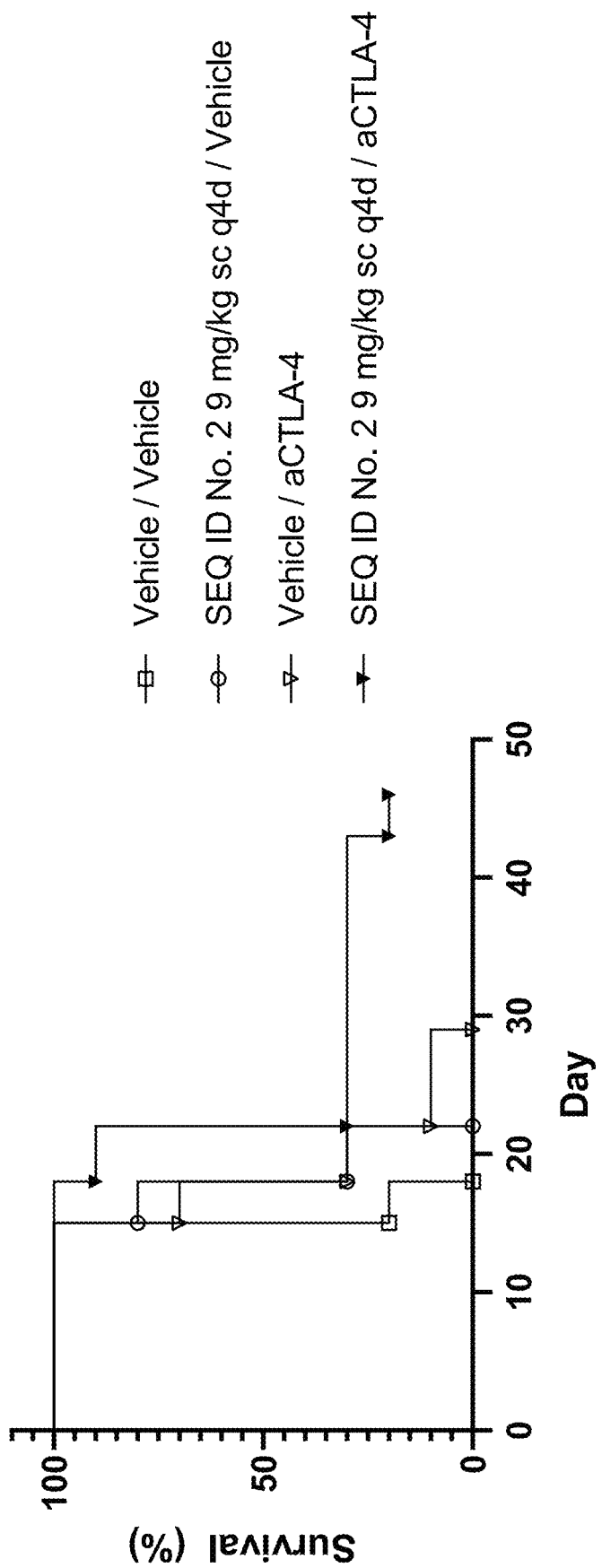

When the fusion protein of SEQ ID NO: 2 was combined with the anti-PD-1 antibody, TGI was increased from 14-17% for monotherapy treatments to 43% for combination therapy (FIG. 8A and FIG. 8B). When the fusion protein of SEQ ID NO: 2 was combined with the anti-PD-1 antibody, TGI was increased from 14-17% for monotherapy treatments to 43% for combination therapy (FIG. 8A and FIG. 8B). When the fusion protein of SEQ ID NO: 2 was combined with the anti-CTLA-4 antibody, TGI was increased from 28-31% for monotherapy treatments to 77% for combination therapy. Combination treatment also resulted in 2 complete responses (FIG. 9A and FIG. 9B).

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

What is claimed is:

1. A method of treating cancer in a patient in need thereof, the method comprising:
   i) administering to the patient a therapeutically effective amount of the fusion protein of SEQ ID NO: 1, or a variant thereof; and
   ii) administering to the patient a therapeutically effective amount of an immune checkpoint inhibitor;
   wherein step (i) is carried out before, after or simultaneously with step (ii), and
   wherein the variant fusion protein is at least 80% identical to full length SEQ ID NO: 1.

2. The method of claim 1, wherein the patient has previously failed to achieve complete or partial response to prior treatment or to ongoing treatment with an immune checkpoint inhibitor as determined by RECIST (Response Evaluation Criteria In Solid Tumors) criteria or according to the irRECIST (immune-related Response Evaluation Criteria In Solid Tumors) criteria.

3. The method of claim 1, wherein the immune checkpoint inhibitor is an anti-PD-1 antibody or an anti PD-L1 antibody, optionally wherein the immune checkpoint inhibitor is pembrolizumab and is optionally:
   administered to the patient at a dose of 200 mg;
   administered to the patient once every three weeks; and/or
   administered intravenously to the patient.

4. The method of claim 1, wherein the immune checkpoint inhibitor is an anti-CTLA4 antibody, optionally wherein the immune checkpoint inhibitor is ipilimumab.

5. The method of claim 1, wherein the fusion protein of SEQ ID NO: 1 or variant thereof is administered parenterally, intravenously, and/or subcutaneously, to the patient.

6. The method of claim 1, wherein a therapeutically effective amount of the fusion protein of SEQ ID NO: 1 or variant thereof is a dose of the fusion protein of SEQ ID NO: 1 or variant thereof of about 0.1 µg/kg, 0.3 µg/kg, 1 µg/kg, 3 µg/kg, 3.5 µg/kg, 4 µg/kg, 4.5 µg/kg, 5 µg/kg, 5.5 µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg, or 14.5 µg/kg.

7. The method of claim 1, wherein the fusion protein of SEQ ID NO: 1 or variant thereof is administered to the patient at a dose of about 3 µg/kg, optionally wherein the fusion protein of SEQ ID NO: 1 or variant thereof is administered intravenously to the patient.

8. The method of claim 1, wherein the fusion protein of SEQ ID NO: 1 or variant thereof is administered to the patient daily for five consecutive days.

9. The method of claim 1, wherein the fusion protein of SEQ ID NO: 1 or variant thereof is administered to the patient at a dose of about 0.3 mg, about 0.6 mg, about 1 mg, about 3 mg, or about 10 mg, optionally wherein the fusion protein of SEQ ID NO: 1 or variant thereof is administered subcutaneously to the patient.

10. The method of claim 9, wherein the fusion protein of SEQ ID NO: 1 or variant thereof is administered to the patient once every week, once every two weeks, or once every three weeks.

11. The method of claim 3, wherein the fusion protein of SEQ ID NO: 1 or variant thereof is administered intravenously to the patient at a dose of about 3 µg/kg daily for five consecutive days, every three weeks, and wherein the pembrolizumab is administered intravenously to the patient at a dose of about 200 mg once every three weeks.

12. The method of claim 3, wherein the fusion protein of SEQ ID NO: 1 or variant thereof is administered subcutaneously to the patient at a dose of about 0.3 mg, about 0.6 mg, about 1 mg, or about 3 mg, once every week and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 0.3 mg, about 0.6 mg, about 1 mg, or about 3 mg, once every week for 6 weeks prior to administration of the pembrolizumab.

13. The method of claim 3, wherein the fusion protein of SEQ ID NO: 1 or variant thereof is administered subcutaneously to the patient at a dose of about 1 mg, about 3 mg, or about 10 mg, once every three weeks and the pembrolizumab is administered intravenously to the patient at a dose of about 200 mg once every three weeks, wherein the fusion protein of SEQ ID NO: 1 or variant thereof is administered subcutaneously to the patient as a monotherapy at a dose of about 1 mg, about 3 mg, or about 10 mg, once every three weeks for 6 weeks prior to administration of the pembrolizumab.

14. The method of claim 1, wherein the patient failed to achieve complete remission (CR) following prior immune checkpoint inhibitor therapy.

15. The method of claim 1, wherein the patient has stable disease (SD), or partial response (PR) with no further reduction in tumor size or response, following prior immune checkpoint inhibitor therapy, optionally wherein the prior immune checkpoint inhibitor therapy comprises one or more of anti-PD-1 therapy, anti-PD-L1 therapy, and anti-CTLA-4 therapy.

16. The method of claim 1, wherein the method results in one or more of the following outcomes for the patient: increased duration of response (DOR);
  increased progression-free survival (PFS); increased time to progression (TTP); and
  increased overall survival (OS), relative to patients receiving the fusion protein of SEQ ID NO: 1 or the immune checkpoint inhibitor as a monotherapy.

17. The method of claim 1, wherein the cancer is selected from the group consisting of squamous cell carcinoma of the head and neck, ovarian cancer, colorectal cancer, melanoma, and breast cancer.

18. The method of claim 1, wherein the patient has previously failed to achieve complete or partial response to prior treatment or to ongoing treatment with an immune checkpoint inhibitor.

19. The method of claim 1, wherein the cancer is recurrent or metastatic squamous cell carcinoma of the head and neck.

* * * * *